US010543259B2

(12) United States Patent
Dauber et al.

(10) Patent No.: US 10,543,259 B2
(45) Date of Patent: Jan. 28, 2020

(54) METHODS AND COMPOSITIONS FOR THE IDENTIFICATION AND TREATMENT OF INDIVIDUALS HAVING OR LIKELY TO DEVELOP SHORT STATURE

(71) Applicant: Children's Hospital Medical Center, Cincinnati, OH (US)

(72) Inventors: Andrew Nahum Dauber, Amberley, OH (US); Vivian Hwa, Cincinnati, OH (US)

(73) Assignee: Children's Hospital Medical Center, Cincinnati, OH (US)

( * ) Notice: Subject to any disclaimer, the term of this patent is extended or adjusted under 35 U.S.C. 154(b) by 90 days.

(21) Appl. No.: 15/015,410

(22) Filed: Feb. 4, 2016

(65) Prior Publication Data

US 2016/0256530 A1 Sep. 8, 2016

Related U.S. Application Data

(60) Provisional application No. 62/126,831, filed on Mar. 2, 2015.

(51) Int. Cl.
| | |
|---|---|
| *A61K 38/18* | (2006.01) |
| *A61K 38/17* | (2006.01) |
| *A61K 48/00* | (2006.01) |
| *C12Q 1/34* | (2006.01) |
| *C07K 14/475* | (2006.01) |
| *C07K 14/47* | (2006.01) |
| *A61K 38/48* | (2006.01) |
| *A61K 9/00* | (2006.01) |
| *C12Q 1/6883* | (2018.01) |

(52) U.S. Cl.
CPC ........ *A61K 38/4886* (2013.01); *A61K 9/0019* (2013.01); *C12Q 1/6883* (2013.01); *A61K 48/00* (2013.01); *C12Q 2600/106* (2013.01); *C12Q 2600/156* (2013.01); *C12Y 304/24* (2013.01)

(58) Field of Classification Search
None
See application file for complete search history.

(56) References Cited

U.S. PATENT DOCUMENTS

2003/0124529 A1* 7/2003 Oxvig ................. C12N 9/6489
435/6.12

OTHER PUBLICATIONS

Bruno et al, Basics and recent advances in peptide and protein drug delivery, Ther Deliv. Nov. 2013 ; 4(11): 1443-1467.*
Fumoto et al, Targeted Gene Delivery: Importance of Administration Routes, Chapter 1, Intech, 2013, pp. 3-31.*
Daya et al, Gene Therapy using Adeno-Associated Virus Vectors, Clin Microbiol Rev, 2008, pp. 583-593.*
Jitendra et al, Noninvasive Routes of Proteins and Peptides Drug Delivery, Indian J Pharm Sci. Jul.-Aug. 2011; 73(4): 367-375.*
Cazares-Delgadillo et al, Human growth hormone: New delivery systems, alternative routes of administration, and their pharmacological relevance, European Journal of Pharmaceutics and Biopharmaceutics 78 (2011) 278-288.*
Dauber et al, Mutations in pregnancy-associated plasma protein A2 cause short stature due to low IGF-I availability, EMBO Mol Med (2016) 8: 363-374.*
Dauber et al, A New Syndrome Associated with Mutations in the Gene for Pregnancy-Associated Plasma Protein A2 (PAPP-A2) Causing Proportionate Short Stature,High Circulating IGF-I, IGFBP-3, and ALS, Mild Microcephaly, thin Long Bones and Decreased Bone Mineral Density in two, ESPE Abstracts, 2015, pp. 1-3.*
Akesh et al, Development of therapeutic proteins: Advances and challenges, Turkish Journal of Biology 39(3) • Jan. 2015.*
Sutradhar et al, Distribution and elimination of protein therapeutics: A review, S. J. Pharm. Sci. 4(2): 01-12.*
Fischer, Future of local bone regeneration—Protein versus gene therapy, Journal of Cranio-Maxillo-Facial Surgery 39 (2011) 54e64.*
Abuzzahab, MJ, et al., "IGF-I Receptor Mutations Resulting in Intrauterine and Postnatal Growth Retardation" The New England Journal of Medicine, 2003, 349(23):2211-22, 12 pgs.
Amselem, S., et al., "Laron Dwarfism and Mutations of the Growth Hormone-Receptor Gene," The New England Journal of Medicine, 1989, 321(15):989-95, 7 pgs.
Baxter, RC, "Insulin-like growth factor (IGF)-binding proteins: interactions with IGFs and intrinsic bioactivities," American Journal of Physiology Endocrinology and Metabolism, 2000, 278(6):E967-76, 10 pgs.
Bayes-Genis, A, et al., "Pregnancy-Associated Plasma Protein A as a Marker of Acute Coronary Syndromes," The New England Journal of Medicine, 2001, 345(14):1022-9, 8 pgs.
Begemann, M, et al., "Paternally Inherited IGF2 Mutation and Growth Restriction," The New England Journal of Medicine, 2015, 373(4):349-56, 8 pgs.
Boldt, HB, et al., "Mutational analysis of the proteolytic domain of pregnancy-associated plasma protein-A (PAPP-A): classification as a metzincin," The Biochemical Journal, 2001, 358(Pt 2):359-67, 9 pgs.
Chen, JW, et al., "A highly sensitive and specific assay for determination of IGF-I bioactivity in human serum," American Journal of Physiology Endocrinology and Metabolism, 2003, 284(6):E1149-55, 7 pgs.

(Continued)

*Primary Examiner* — Maria Marvich
(74) *Attorney, Agent, or Firm* — Frost Brown Todd LLC; Nicole M. Tepe

(57) ABSTRACT

The instant disclosure relates to methods useful for the treatment or prevention of progressive growth failure in a subject in need thereof. The method may include the step of administering a PAPPA2 gene product to the subject. Also disclosed is the identification of a novel gene mutation that may be used as a marker to identify subjects particularly suited for such treatment. Compositions containing a therapeutically effective amount of PAPPA2 protein and a pharmaceutically acceptable carrier are also disclosed.

6 Claims, 12 Drawing Sheets

Specification includes a Sequence Listing.

(56) References Cited

OTHER PUBLICATIONS

Christians, JK, et al., "PAPPA2, an Enzyme That Cleaves an insulin-Like Growth-Factor-Binding Protein, Is a Candidate Gene for a Quantitative Trait Locus Affecting Body Size in Mice," Genetics, 2006, 173(3):1547-53, 7 pgs.
Christians, JK, et al., "Pregnancy Associated Plasma Protein A2 (PAPP-A2) Affects Bone Size and Shape and Contributes to Natural Variation in Postnatal Growth in Mice," PloS One, 2013, 8(2):e56260, 10 pgs.
Conover, CA, et al., "Pregnancy-Associated Plasma Protein-A2 (PAPP-A2): Tissue Expression and Biological Consequences of Gene Knockout in Mice," Endocrinology, 2011, 152(7):2837-44, 8 pgs.
David, A., et al., "Evidence for a Continuum of Genetic, Phenotypic, and Biochemical Abnormalities in Children with Growth Hormone Insensitivity," Endocrine Reviews, 2011, 32(4):472-97, 26 pgs.
Domene, HM, et al., "Deficiency of the Circulating Insulin-like Growth Factor System Associated with Inactivation of the Acid-Labile Subunit Gene," The New England Journal of Medicine, 2004, 350(6):570-7, 8 pgs.
Gyrup, C, et al., "Quantitative Analysis of Insulin-like Growth Factor-Modulated Proteolysis of Insulin-like Growth Factor Binding Protein-4 and -5 by Pregnancy-Associated Plasma Protein-A," Biochemistry, 2007 46(7):1972-80, 9 pgs.
Ho, S.N., et al., "Site-directed mutagenesis by overlap extension using the polymerase chain reaction," Gene, 1989, 77(1):51-9, 9 pgs.
Kjaer-Sorensen, K, et al., "Papp-a2 modulates development of cranial cartilage and angiogenesis in zebrafish embryos," Journal of Cell Science, 2014, 127(23):5027-5037, 11 pgs.
Kloverpris, S, et al., "A robust immunoassay for pregnancy-associated plasma protein-A2 based on analysis of circulating antigen: establishment of normal ranges in pregnancy," Molecular Human Reproduction, 2013, 19(11):756-63 8 pgs.
Kofoed, EM, et al., "Growth Hormone Insensitivity Associated with a STAT5b Mutation," The New England Journal of Medicine, 2003, 349(12):1139-47, 9 pgs.
Lango Allen, H, et al., "Hundreds of variants clustered in genomic loci and biological pathways affect human height," Nature, 2010, 467(7317):832-8, 7 pgs.
Laursen, LS, et al., "Real-time measurement in living cells of insulin-like growth factor activity using bioluminescence resonance energy transfer," Biochemical Pharmacology, 2005, 69(12):1723-32, 10 pgs.
Laursen, LS, et al., "Regulation of Insulin-Like Growth Factor (IGF) Bioactivity by Sequential Proteolytic Cleavage of IGF Binding Protein-4 and -5," Molecular Endocrinology, 2007 21(5):1246-57, 12 pgs.

Malone, FD, et al., "First-Trimester or Second-Trimester Screening, or Both, for Down's Syndrome," The New England Journal of Medicine, 2005, 353(19):2001-11, 11 pgs.
Modric, T, et al., "Phenotypic Manifestations of Insulin-Like Growth Factor-Binding Protein-3 Overexpression in Transgenic Mice," Endocrinology, 2001, 142(5):1958-67, 10 pgs.
Overgaard, MT, et al., "Expression of Recombinant Human Pregnancy-Associated Plasma Protein-A and identification of the Proform of Eosinophil Major Basic Protein as Its Physiological Inhibitor," The Journal of Biological Chemistry, 2000, 275(40):31128-33, 7 pgs.
Overgaard, MT, et al., "Pregnancy-associated Plasma Protein-A2 (PAPP-A2), a Novel Insulin-Like Growth Factor-Binding Protein-5 Proteinase," The Journal of Biological Chemistry 2001 276(24):21849-53, 6 pgs.
Oxvig, C., "The role of PAPP-A in the IGF system: location, location, location," Journal of Cell Communication and Signaling, 2015, 9:177-187, 11 pgs.
Pear, WS, et al., "Production of high-titer helper-free retroviruses by transient transfection," Proceedings of the National Academy of Sciences of the United States of America, 1993, 90(18):8392-6, 5 pgs.
Reinhard, M, et al., "Effect of hyperinsulinemia during hemodialysis on the insulin-like growth factor system and inflammatory biomarkers: a randomized open-label crossover study," BMC Nephrology, 2013, 14:80, 12 pgs.
Sorensen, JS, et al., "Residual beta-cell Function and the Insulin-Like Growth Factor 1 System in Danish Children and Adolescents with Type 1 Diabetes," The Journal of Clinical Endocrinology and Metabolism, 2015, 100(3):1053-61.
Winn, VD, et al., "Severe Preeclampsia-Related Changes in Gene Expression at the Maternal-Fetal Interface Include Sialic Acid-Binding Immunoglobulin-Like Lectin-6 and Pappalysin-2," Endocrinology, 2009 150(1):452-62, 11 pgs.
Wood, AR, et al., "Defining the role of common variation in the genomic and biological architecture of adult human height," Nature Genetics, 2014, 46(11):1173-86, 18 pgs.
Woods, KA, et al., "Intrauterine Growth Retardation and Postnatal Growth Failure Associated With Deletion of the Insulin-Like Growth Factor I Gene," The New England Journal of Medicine, 1996, 335(18):1363-75 pgs.
Yakar, S., et al., "Circulating levels of IGF-1 directly regulate bone growth and density," The Journal of Clinical Investigation, 2002, 110(6):771-81, 11 pgs.
Yan, X, et al., "Involvement of Pregnancy-Associated Plasma Protein-A2 in Insulin-Like Growth Factor (IGF) Binding Protein-5 Proteolysis During Pregnancy: A Potential Mechanism for Increasing IGF Bioavailability," The Journal of Clinical Endocrinology and Metabolism, 2010, 95(3):1412-20, 9 pgs.
Zhang, M, et al., "Osteoblast-specific Knockout of the Insulin-like Growth Factor (IGF) Receptor Gene Reveals an Essential Role of IGF Signaling in Bone Matrix Mineralization," The Journal of Biological Chemistry, 2002, 277(46):44005-12, 9 pgs.

* cited by examiner

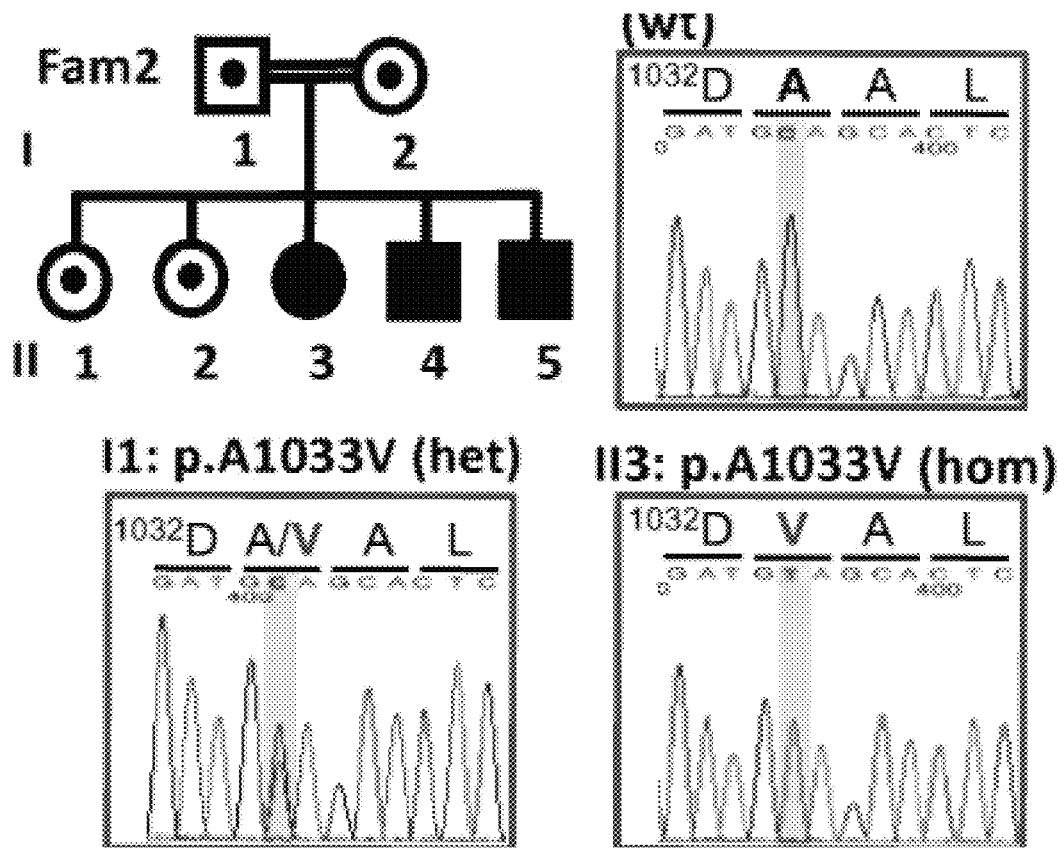

METHODS AND COMPOSITIONS FOR THE IDENTIFICATION AND TREATMENT OF INDIVIDUALS HAVING OR LIKELY TO DEVELOP SHORT STATURE

CROSS-REFERENCE TO RELATED APPLICATIONS

This application claims the benefit of and priority to U.S. Provisional Application 62/126,831, filed Mar. 2, 2015, entitled "Enzyme replacement therapy of PAPP-PA2," the contents of which is incorporated herein it its entirety for all purposes.

STATEMENT REGARDING FEDERALLY SPONSORED RESEARCH OR DEVELOPMENT

This invention was made with government support under HD073351 awarded by the National Institutes of Health. The government has certain rights in the invention.

BACKGROUND OF THE INVENTION

The term idiopathic short stature (ISS) refers to short children with no identifiable disorder of the growth hormone (GH)/insulin like growth factor (IGF) axis and no other endocrine, genetic or organ system disorder. This heterogeneous group of short children without GH deficiency (GHD) includes children with constitutional delay of growth and puberty, familial short stature, or both, as well as those with subtle cartilage and bone dysplasias. ISS can be defined as a condition characterized by a height more than 2 standard deviations below the corresponding average height for a given age, sex and population, without findings of disease. Approximately 80% of all children referred for short stature will be labeled as ISS. ISS can be considered as part of the continuum extending from complete growth hormone deficiency (GHD) to normality and covering different degrees of GH secretion and responsiveness.

ISS has recently been subdivided into two major groups: a) familial short stature (FSS), when the child is short compared with the reference population, but remains within the range of target height; b) non-familial short stature (NFSS), when the child is short both in comparison with the reference population and the target height. This latter subgroup inevitably includes short children with constitutional delay of growth and puberty (CDGP).

Currently, the only approved therapy for ISS is recombinant human growth hormone therapy. Individual patient responsiveness to growth hormone is quite variable with some patients receiving no benefit in terms of increased growth velocity. By definition, these patients have normal growth hormone secretion but have a limitation in their growth response to both endogenous and exogenous growth hormone. Alternative therapies which seek to improve the downstream growth hormone signaling pathway are needed. Additionally, growth hormone is approved for patients born small for gestational age with lack of catch up growth. These patients are also variably responsive to growth hormone therapy and are in need of additional therapeutic options. Thus, while a significant percentage of the population suffers from ISS or other conditions that result in short stature, there are currently limited tools to identify candidates that are likely to be successfully treated for short stature using specific treatments, and limited treatments available for individuals suffering from ISS or short stature of known causes. The instant disclosure seeks to address one or more needs in the art.

BRIEF SUMMARY OF THE INVENTION

The instant disclosure relates to methods useful for the treatment or prevention of progressive growth failure in a subject in need thereof. The method may include the step of administering a PAPPA2 gene product to the subject. Also disclosed is the identification of a novel gene mutation that may be used as a marker to identify subjects particularly suited for such treatment. Compositions containing a therapeutically effective amount of PAPPA2 protein and a pharmaceutically acceptable carrier are also disclosed.

BRIEF DESCRIPTION OF THE DRAWINGS

FIG. 1A depicts Family 1-Subject II.1. FIG. 1B depicts Family 1-Subject II.3.

FIG. 1C depicts Family 2-Subject II.3. FIG. 1D depicts Family 2-Subject II.4. FIG. 1E depicts Family 2-Subject II.5. FIG. 1F Top Row Representative X-rays showing narrow fibulae and elongated digits in Subject II.1 of Family 1. Bottom Row—Lower extremities and foot from Subject II.5 and hand from Subject II.4, both from Family 2.

FIG. 2A-FIG. 2C: PAPPA2 Gene and Family Pedigrees. FIGA: Schematic representation of the genomic structure of the PAPPA2 gene on chromosome band 1q24, the encoded mRNA and the protein with its relevant functional domains. Red stars indicate the location in the exons, mRNA and protein where the subjects' mutations are found. FIG. 2B: Pedigree and representative Sanger sequencing trace of the mutation identified in family 1. FIG. 2C: Pedigree and representative Sanger sequencing trace of the mutation identified in family 2.

FIG. 3 A shows an assessment of proteolytic activity present in culture media of cells transfected with cDNA encoding PAPP-A2, PAPP-A2(D643fs) (family 1), or PAPP-A2(A1033V) (family 2). Radiolabeled substrates tested 17 include IGFBP-3, IGFBP-4, and IGFBP-5. Cleavage was visualized by autoradiography following SDS-PAGE. Positions of intact IGFBPs (i) and cleavage products (c) are indicated. FIG. 3B depicts western blots following nonreducing or reducing SDS-PAGE of media from transfected cells, as indicated. Polyclonal antibodies raised against the N-terminal portion of PAPP-A2 were used for detection. FIG. 3C depicts a comparison of proteolytic activity similar to the experiment of FIG. 3A, except that equimolar concentrations of PAPP-A2 and PAPP-A2 (A1033V) were used. The variant from Family 1, carrying a frameshift mutation N-terminal to the proteolytic domain of PAPP-A2, did not show any detectable expression. All gels and blots are representative of three independent experiments.

FIG. 4A depicts levels of endogenous insulin-like growth factor (IGF)-I in the different fractions obtained by neutral chromatography on a Superdex 200 column. Serum samples from the four siblings of family 1 were analyzed and compared to a non-related prepubertal control, as all siblings were prepubertal. The amount of IGF-I detected in the fractions corresponding to the ternary complex (TC) was markedly greater in the homozygous affected subjects (11.1 and 11.3) compared to the unaffected siblings (11.2 and 11.4) and the prepubertal control. No IGF-I was detected in the fractions corresponding to the binary complex (BC) or free IGF-I in any of the subjects. This is most likely due to the fact that under physiological conditions 80-85% of IGF-I circulates in the TC and after the separation procedure, the amount of IGF-I in the BC or free was below the level of detection of our IGF-I assay. These results clearly demonstrate that in the affected patients the amount of IGF-I circulating in the TC is markedly elevated. FIG. 4B depicts a cartoon of hypothesized mechanism underlying growth failure due to lack of PAPP-A2. There is an increase in the formation of ternary complexes, due to decreased proteolysis subsequent to the lack of PAPP-A2 activity. This results in reduced levels of free IGF-I (fIGF-I) in serum and most likely at specific target tissues. This also decreases the negative feedback effect of IGF-I on growth hormone (GH) production, contributing to the increased circulating levels of GH. Increased serum GH levels cause increased IGF-I, IGFBP-3 and ALS levels. This increase in IGFBP-3 and ALS would then contribute to further ternary complex formation and an increase in total IGF-I and IGF-II levels.

DETAILED DESCRIPTION OF THE INVENTION

Definitions

Figure 1A:
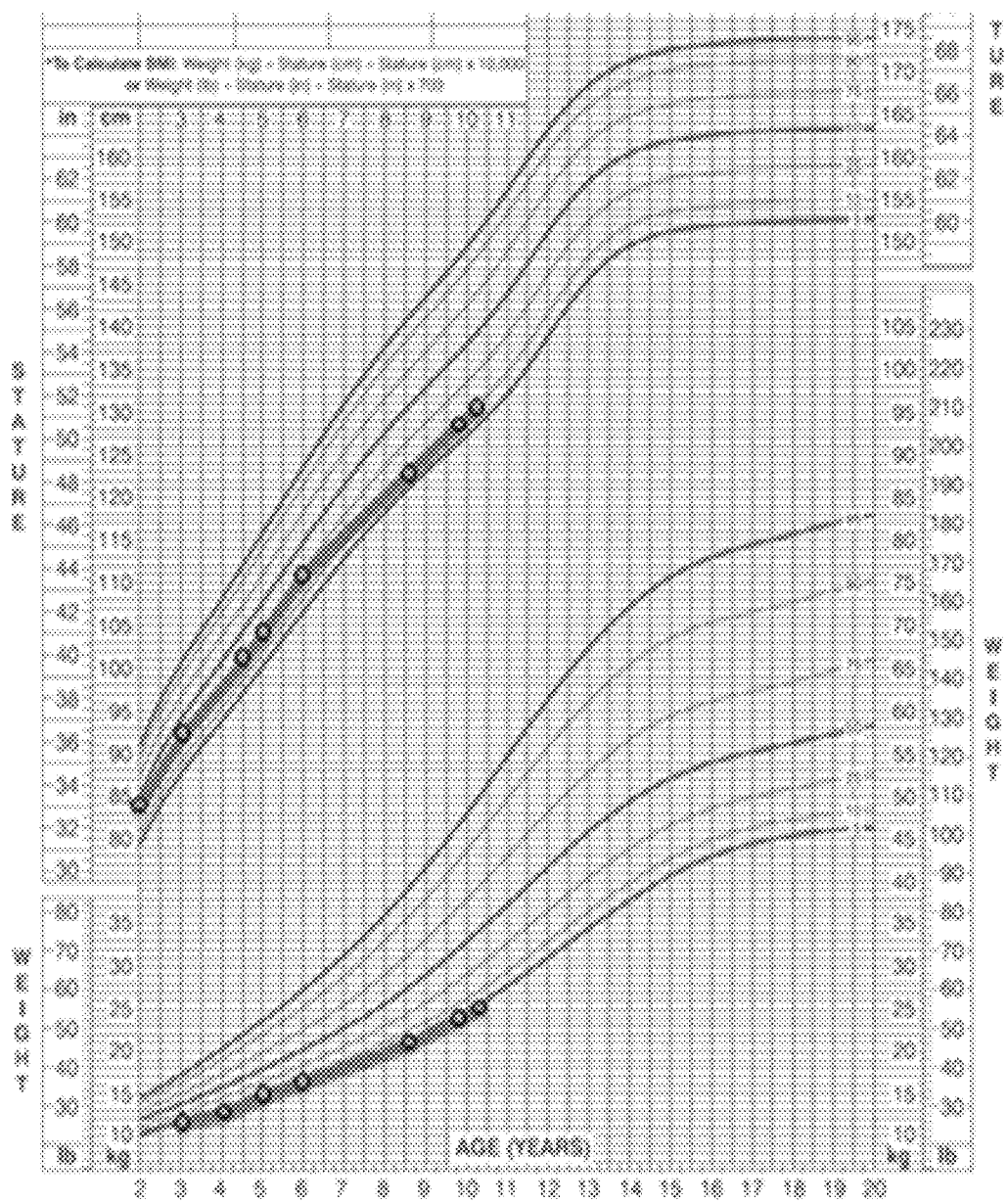
FIG. 1A-FIG. 1F show growth charts of affected subjects.
Figure 1B:
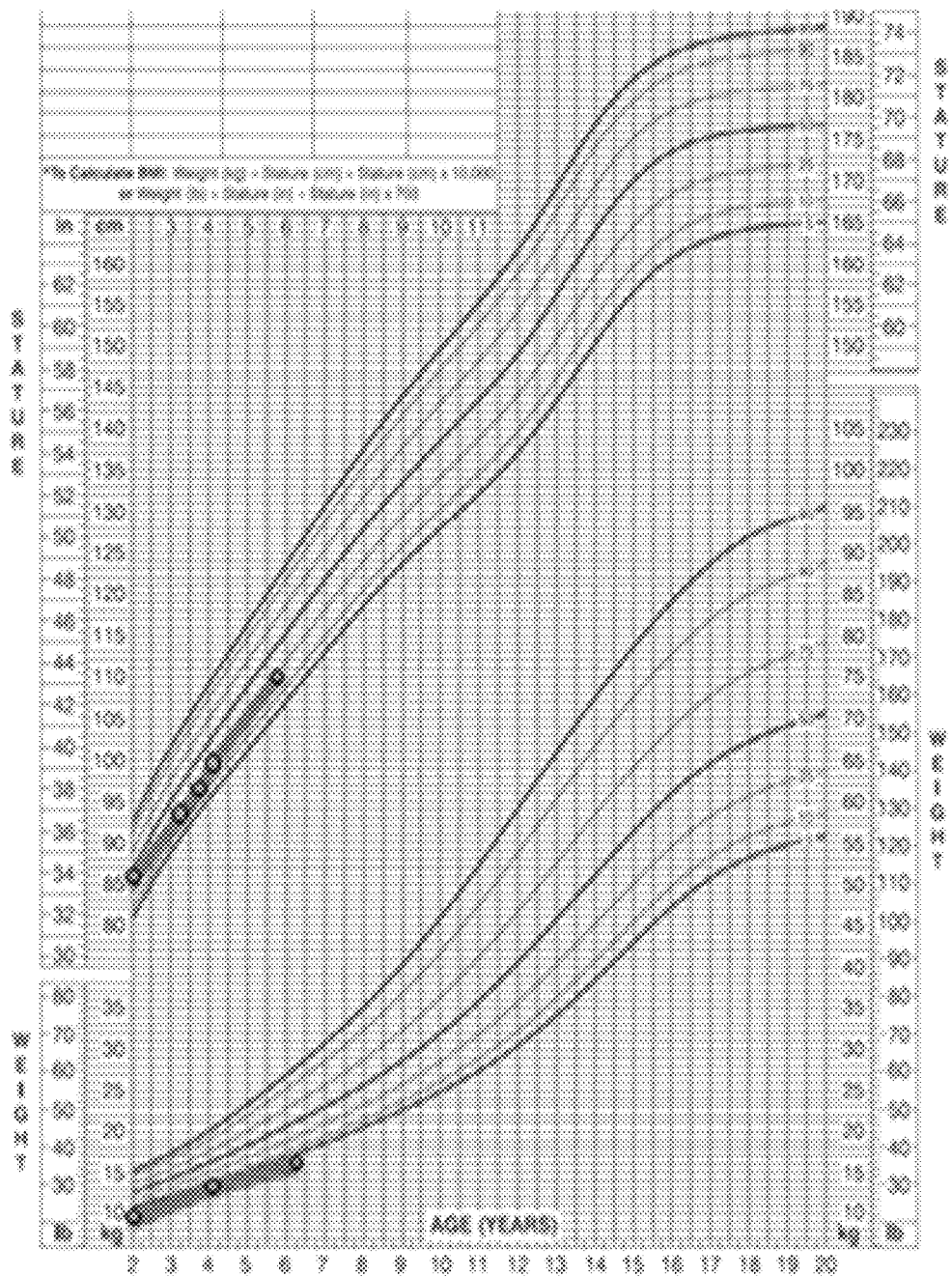
Figure 1C:
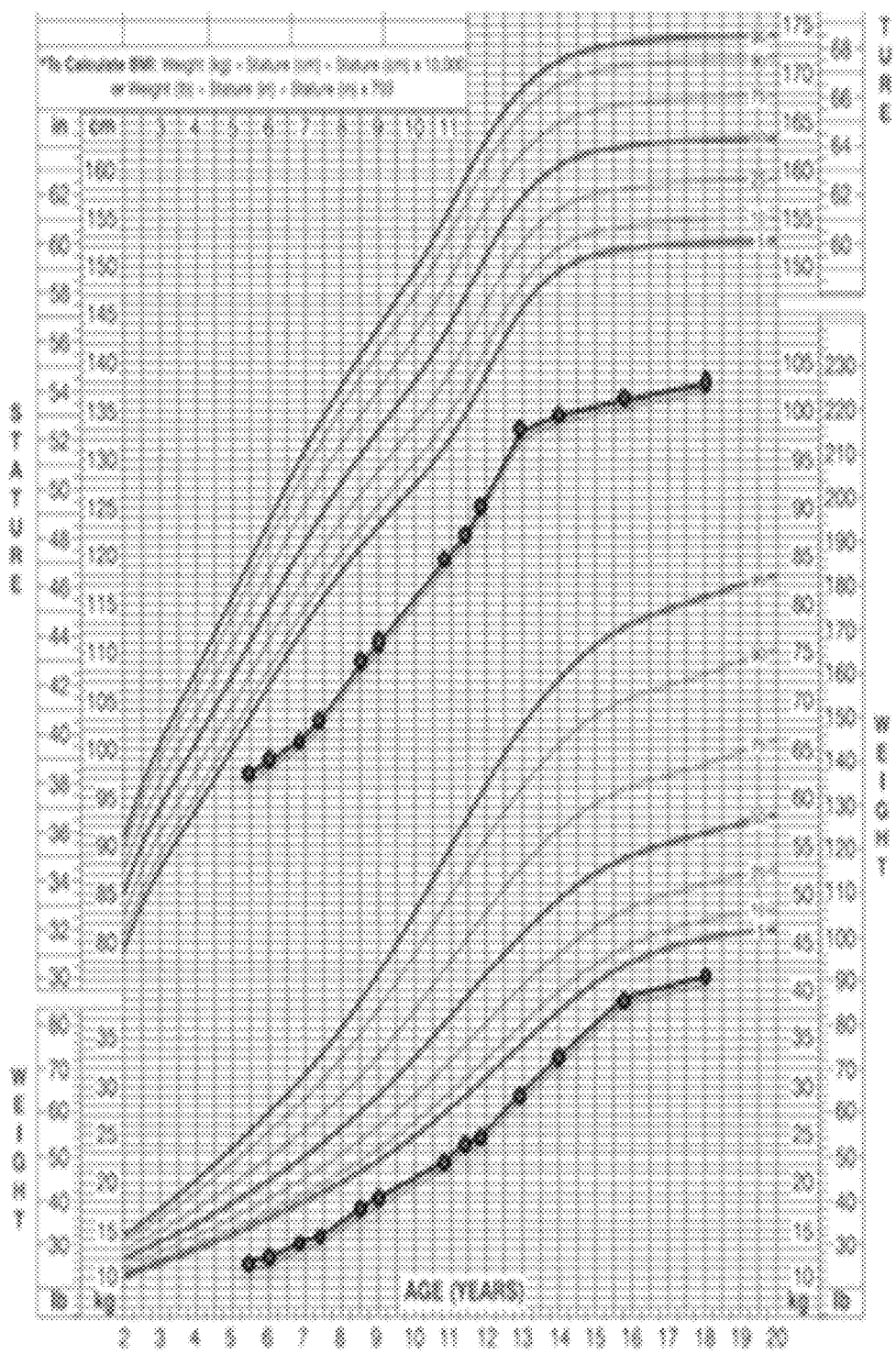
Figure 1D:
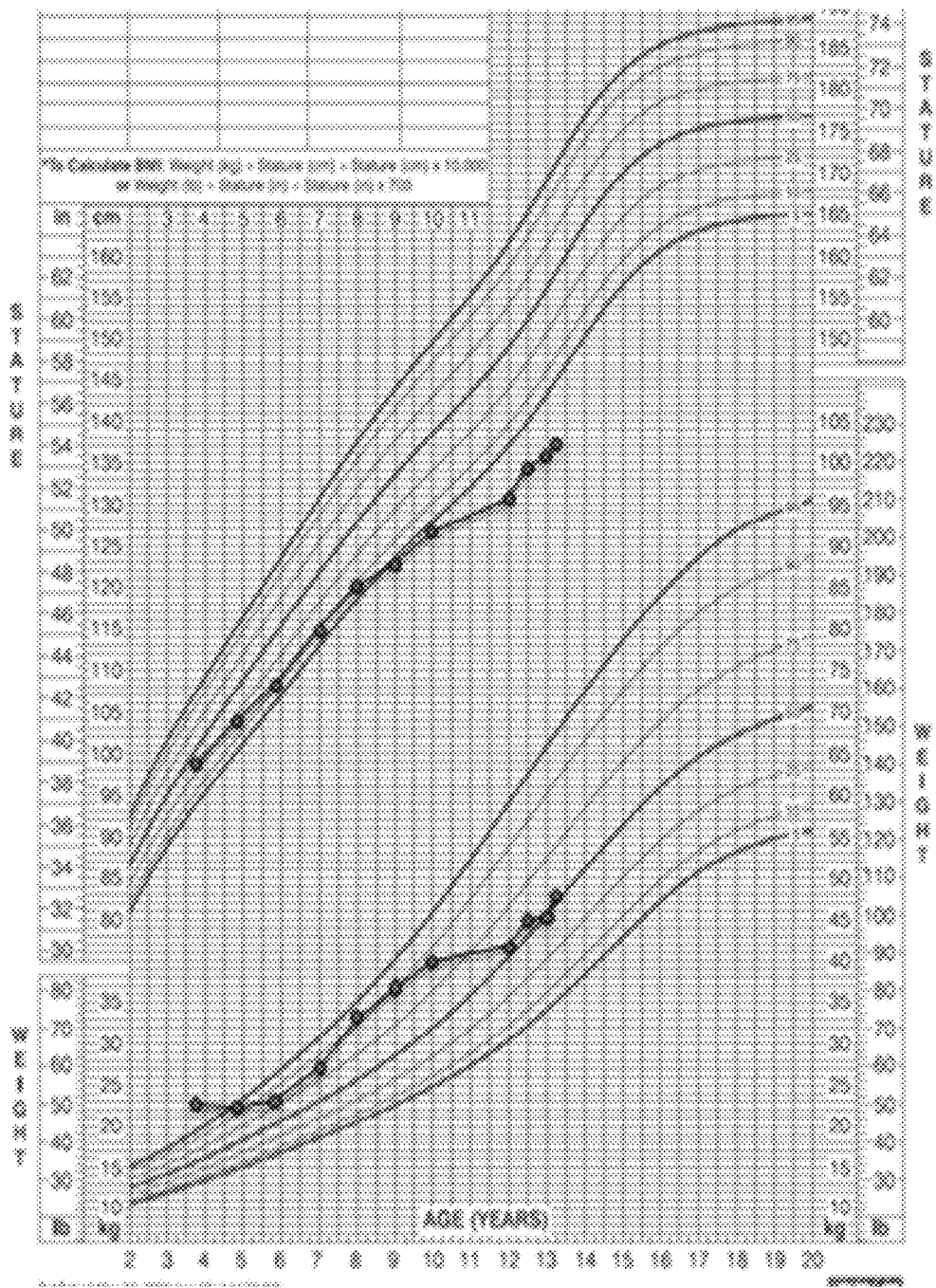
Figure 1E:
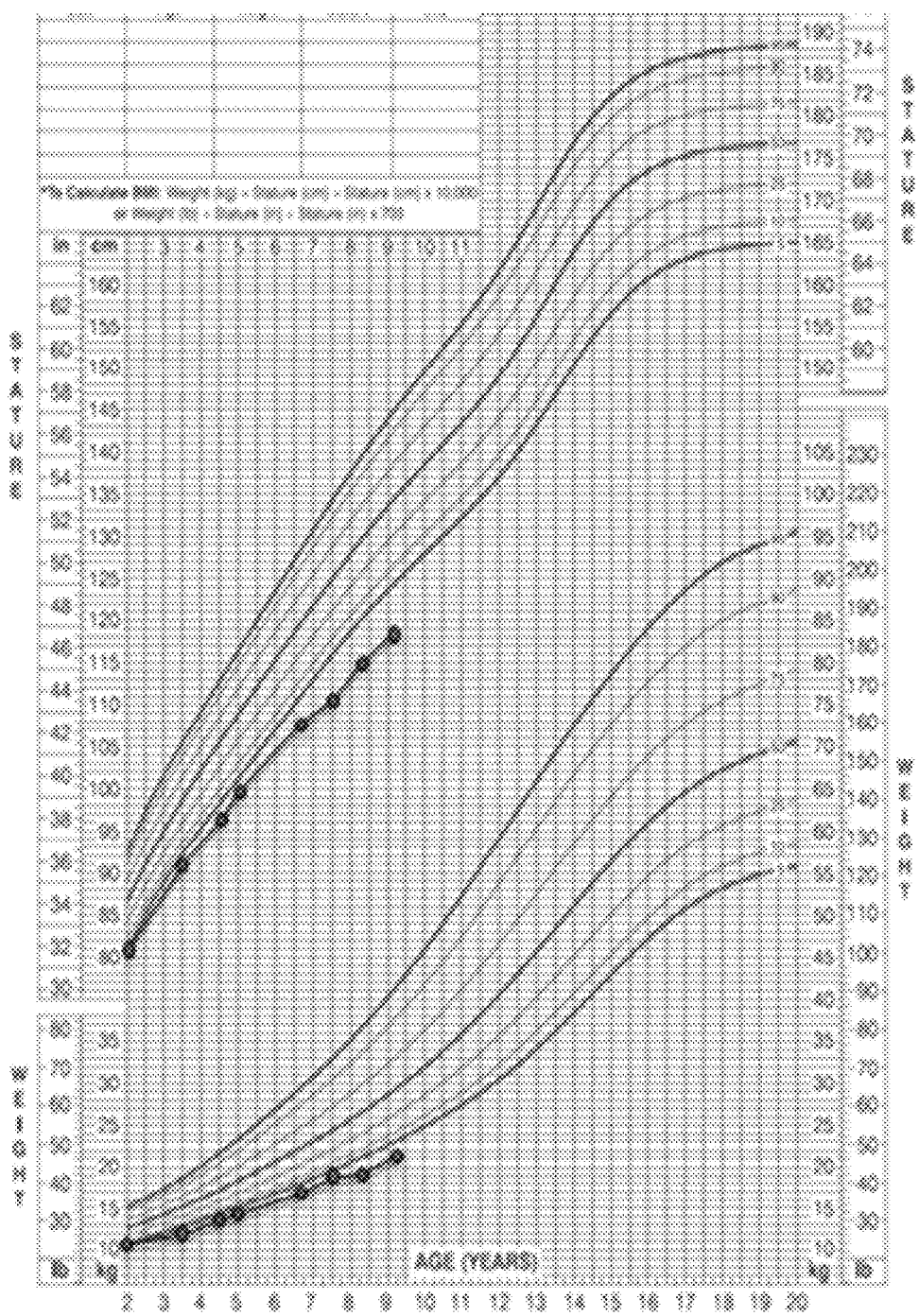
Figure 1F:
Figure 2A:
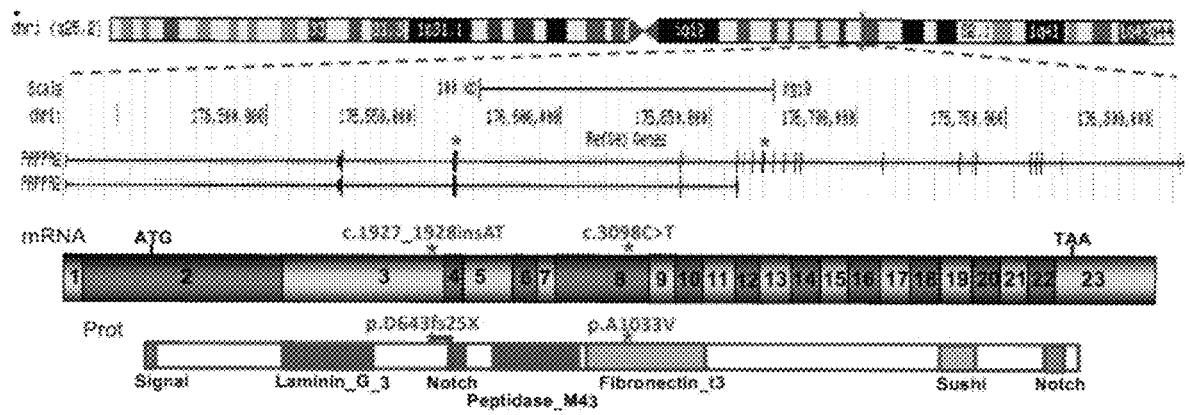
Figure 2B:
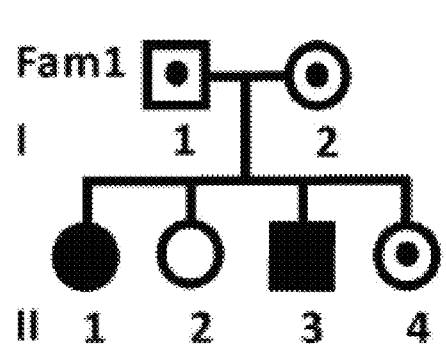
Figure 2B:
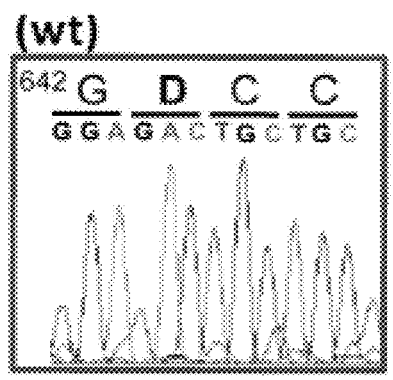
Figure 2B:
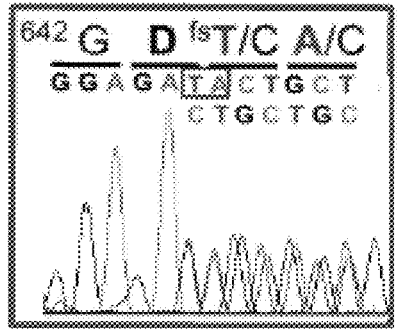
Figure 2B:
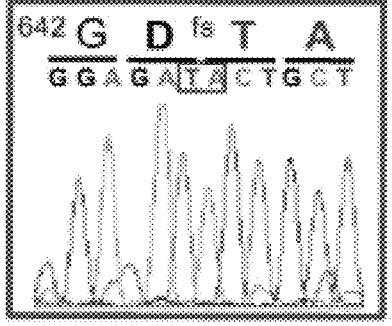

The term "purified" as used herein refers to material that has been isolated under conditions that reduce or eliminate the presence of unrelated materials i.e., contaminants, including native materials from which the material is obtained. For example, a purified protein is preferably substantially free of other proteins or nucleic acids with which it is associated in a cell; a purified nucleic acid molecule is preferably substantially free of proteins or other unrelated nucleic acid molecules with which it can be found within a cell. As used herein, the term "substantially free" is used operationally, in the context of analytical testing of the material. Preferably, purified material substantially free of contaminants is at least 95% pure; more preferably, at least 97% pure, and more preferably still at least 99% pure. Purity can be evaluated by chromatography, gel electrophoresis, immunoassay, composition analysis, biological assay, and other methods known in the art. In a specific embodiment, purified means that the level of contaminants is below a level acceptable to regulatory authorities for administration to a human or non-human animal.

The terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated.

As used herein, catch-up growth is characterized by an increase in height velocity in the first two years of life resulting in a child who was born small for gestational age reaching a height at or above the 5$^{th}$ percentile by two years of age.

A "gene" is a sequence of nucleotides which code for a functional "gene product".

The terms "therapeutically effective dose" and "effective amount" refer to the amount of the compound that is sufficient to result in a therapeutic response. A therapeutic response may be any response that a user (e.g., a clinician) will recognize as an effective response to the therapy. Thus, a therapeutic response will generally be an amelioration of one or more symptoms of a disease or disorder.

The growth hormone (GH)/insulin-like growth factor (IGF)-I system is essential for correct human growth. GH promotes growth via IGF-I production and by direct actions on the growth plate. IGF-I circulates bound to six IGF binding proteins (IGFBPs). After binding IGF, IGFBP-3 and -5 also bind with the IGF acid labile subunit (ALS) to form a ternary complex, which further increases IGF-I's half-life.[1] Free IGF-I ("fIGF-I") binds its receptor, activating signaling cascades that up-regulate multiple genes fundamental to growth.[2] Human genetic defects in this axis lead to syndromes marked by impaired growth and have helped to further our understanding of growth physiology.[3] GH receptor (GHR) mutations have been shown to cause Laron syndrome with extreme growth failure.[4] Mutations in the STAT5B5, IGF-I6 and IGF-I receptor (IGF-IR)[7] genes cause varying degrees of pre- and post-natal growth retardation and mutations in ALS cause mild short stature.[8] The first mutation in IGF2 affecting pre- and post-natal growth was recently identified.[9] To date, no human mutations in the six high-affinity IGFBPs or their regulatory proteins have been reported in association with a monogenic syndrome.

As disclosed herein, Applicant has identified a novel genetic defect associated with growth failure, and a novel treatment option for both subjects having the identified genetic defect and subjects suffering from short stature that do not have such genetic defect. In particular, Applicant has identified two families with homozygous loss-of-function mutations in PAPPA2, a gene encoding pregnancy-associated plasma protein-A2 (PAPP-A2), a protease highly specific for IGFBP-3 and -5[10], resulting in a novel syndrome of growth retardation with markedly elevated circulating IGF-I and IGF-II, but decreased fIGF-I levels and IGF bioactivity. Specifically, Applicant has found a novel missense mutation in PAPPA2 (Ala1033Val), Accession number NP_064714, associated with progressive growth failure.

The PAPPA2 gene product, which is a protease, is believed to be responsible for cleaving IGF binding partners that normally sequester (or render unavailable) IGF. Cleavage of the IGF binding proteins results in increased serum free IGF ("fIGF"). Free IGF, in turn, stimulates and/or enhances growth in an individual, particularly prior to or during puberty. Without intending to be limited by theory, it is believed that exogenous administration of a functional PAPPA2 protease to an individual having a mutation in the PAPPA2 gene, wherein such mutation results in a full or partial loss of function in the PAPPA2 gene improves growth in the individual. In other aspects, the PAPPA2 protease may be administered to any individual diagnosed with short stature, regardless of the presence or absence of a mutation in the PAPPA2 gene or compromised PAPPA2 function, including patients born small for gestational age with lack of catch up growth. PAPPA2 administration should lead to increased levels of endogenous fIGF thereby further promoting growth.

Applicant has identified two families with a novel syndrome of progressive growth failure with markedly elevated serum concentrations of IGF-I, IGFBP-3 and -5 resulting from loss of PAPP-A2 function. PAPP-A2, a member of the pappalysin family of metzincin metalloproteinases, is closely related to PAPP-A, a protease that targets IGFBP- 4.[12] While PAPP-A has been extensively studied due to its biomarker roles[13,14], the function of PAPP-A2 in human physiology is largely unknown. Prior in vitro work has shown that PAPP-A2 specifically cleaves IGFBP-3 and -5 with no activity towards other IGFBPs.[10] Applicant has shown that loss of PAPP-A2 function leads to increased serum concentrations of IGFBP-3 and -5 resulting in increased total IGF-I levels. Total IGF-II is also elevated, consistent with the increased ALS and IGFBP-3 levels. However, this increase in total IGFs was not accompanied by an elevated ability of serum to activate IGF-IR in vitro (IGF bioactivity). Without intending to be limited by theory, it is believed that this relative decrease in IGF bioactivity is due to an inability of abnormal PAPP-A2 to liberate IGF-I from its binding partners resulting in decreased fIGF-I. The primary site of action for PAPP-A2 is unknown. Unlike PAPP-A, PAPP-A2 is not membrane bound and does not require the presence of IGF-I for its proteolytic function.[10]

Figure 4A:
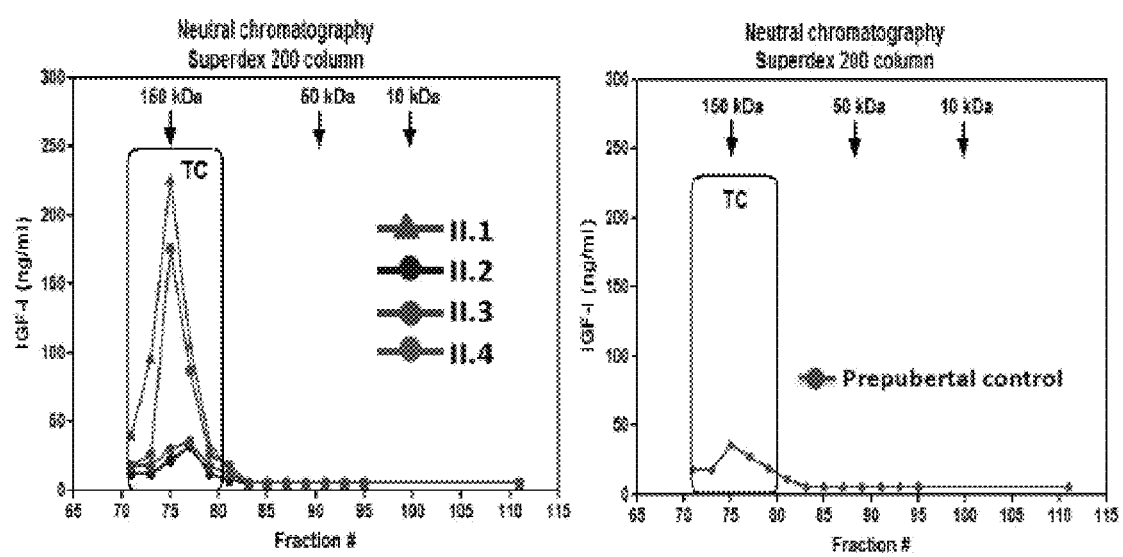
FIG. 4A-4B depicts IGF-I neutral chromatography and proposed mechanism of action of PAPP-A2 deficiency.
Figure 4B:
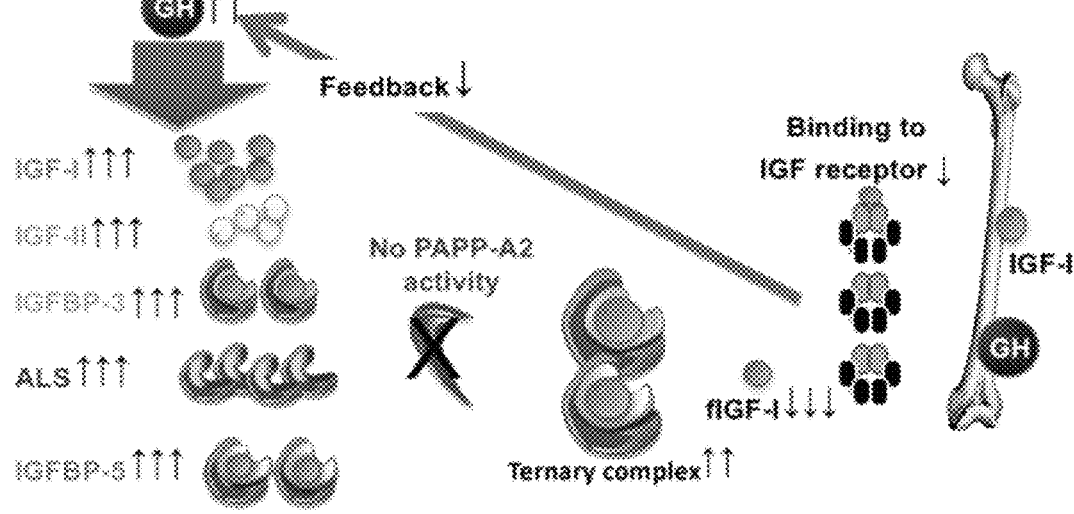

Growth failure may be due to a systemic effect or a defect in PAPP-A2 function at the tissue level, in particular at the growth plate. Aspects of the patients' phenotype could be due to direct effects of the increased IGFBPs. Interestingly, GH is elevated in the patients, resulting in increased levels of all GH-dependent factors (IGF-I, IGFBP-3, IGFBP-5 and ALS). It is believed that, without intending to be limited by theory, that the rise in GH is due to decreased negative feedback consequent to low fIGF-I levels (FIG. 4B). Thus, Applicant's data indicates that PAPP-A2 is a key regulator of human growth and IGF-I bioavailability by regulating the proportion of IGF-I that is either free or bound to its IGFBPs.

Mouse models of PAPP-A2 deficiency have striking similarities to the patients studied, as Pappa2(−/−) mice recapitulate the human biochemical phenotype with elevated total IGF-I and low fIGF-I levels. Pappa2(−/−) mice exhibit a trend towards decreased birth weight and significant post-natal growth retardation[11,15] which correlates with Applicant's findings as the patients were born mildly small for gestational age and exhibited the most prominent growth failure postnatally. Indeed, progressive post-natal growth retardation occurred in all affected individuals, becoming more prominent with age. While the range in the absolute heights of the affected patients is wide, subjects in family one are quite discordant from their target mid-parental height and it is yet to be seen if their growth failure becomes progressively worse with age, as seen in family two. PAPP-A2 is responsible for the proteolysis of IGFBP-5 during pregnancy resulting in increased fIGF-I,[16] but how this affects fetal growth and development in normal individuals and in the studied subjects is unknown. Lack of PAPP-A2 led to decreased length of the mandible, skull, femur, pelvic girdle and tailbone in mice[15] and severely reduced cranial cartilages in zebrafish.[17]

The subjects studied had small chins, long thin fingers, thin femurs and moderate microcephaly. In the two subjects undergoing DXA, one showed mild osteoporosis and the other osteopenia. Mice with blunted IGF-I activity in osteoblasts show defects in bone mineralization during postnatal growth.[18] Transgenic mice over-expressing IGFBP-3[19] have modest pre- and post-natal growth retardation despite high IGF-I levels, presumably reflecting reduced fIGF-I, as seen in our patients.

The gene encoding PAPP-A2 was located in a quantitative trait locus for body size in mice[20] and PAPP-A2 was confirmed to be partially responsible for the effect of this locus.[15] A SNP located in close proximity to human PAPPA2 (rs1325596) was recently identified in a large genome-wide association study as being correlated with height in the general population.[21,22] Thus, common genetic variants in PAPPA2 may have mild effects on growth, while rare loss-of-function variants, such as those seen in our subjects, have a more pronounced effect.

In conclusion, Applicant has identified a new syndrome in two unrelated families with loss-of-function variants in PAPPA2 resulting in progressive growth failure, moderate microcephaly, thin long bones, a marked elevation of total IGF-I levels due to impaired proteolysis of IGFBP-3 and -5, and reduced fIGF-I. These patients represent the first human cases of diminished IGF-I bioavailability due to defects in IGFBP regulation, indicating that PAPP-A2 is a key regulator of IGF-I bioavailability and that deregulated IGFBP proteolysis can have relevant consequences in human physiology. These results also emphasize the potential importance of proteins that interact with PAPP-A2[23] that have been previously shown to affect human height.[21] Thus, patients currently labeled as idiopathic short stature with elevated IGF-I and IGFBP-3 concentrations could conceivably obtain a specific diagnosis after undergoing testing for mutations in PAPPA2, or possibly in proteins that regulate the activity of this protease. Indeed, the data presented here indicate that understanding PAPP-A2 regulation and function will have important implications in both the clinical diagnosis of growth retardation and other areas of IGF-I biology.

Methods

Disclosed herein are methods of treating progressive growth failure in a subject in need thereof. In one aspect, the method may comprise the step of administering a PAPPA2 gene product to the subject.

In one aspect, the subject in need thereof may be diagnosed with idiopathic short stature or is identified as small for gestational age without catch up growth.

In one aspect, the subject in need thereof may have a loss-of-function mutation in a PAPPA2 gene.

In one aspect, the subject in need thereof may have a heterozygous loss-of-function mutation in a PAPPA2 gene.

In one aspect, the subject in need thereof may have a homozygous loss-of-function mutation in a PAPPA2 gene.

In one aspect, the subject in need thereof may have a homozygous or heterozygous mutation in a PAPPA2 gene that results in decreased function of PAPPA2 protein in vivo.

In one aspect, the subject in need thereof may have a homozygous or heterozygous mutation in a PAPPA2 gene that results in decreased function of PAPPA2 protein as measured in vitro, as determined by the ability of isolated PAPPA2 from said patient to cleave IGFBPs, preferably IGFBP-3, and IGFBP-5.

In one aspect, the subject in need thereof may be normal PAPPA2 protein function.

In one aspect, the method may comprise the step of administering to said subject a PAPPA2 gene product during puberty, prior to puberty, or both, wherein said gene product retains at least 80% PAPPA2 enzyme function, or at least 85% PAPPA2 enzyme function, or at least 90% PAPPA2 enzyme function, or at least 95% PAPPA2 enzyme function.

In one aspect, the subject in need thereof may have increased serum IGF-I levels as compared to individuals of normal stature, wherein said increased serum IGF-1 concentration are measured during puberty, prior to puberty, or both.

In one aspect, the subject in need thereof may have decreased free IGF-1 levels as compared to an individual of normal stature.

In one aspect, the subject in need thereof may have a height of about two standard deviations below the mid-parental target height, or about 2.25 standard deviations below normal, or greater than 2.25 standard deviations below normal, or greater than 3 standard deviations below normal.

In one aspect, the method may comprise the step of administering the PAPPA2 gene product via a route selected from intravenously, subcutaneously, intramuscularly, or a combination thereof.

In one aspect, the method may comprise the step of administering the PAPPA2 gene product in a form for extended-release, for example in an implantable bio-erodable solid.

In one aspect, the method may comprise the step of administering the PAPPA2 gene product in vivo by administration to said subject a recombinant vector containing a nucleic acid sequence that encodes said functional PAPPA2 gene product.

In a further aspect, the method may comprise the step of administering a composition as disclosed herein, for example, a composition comprising a PAPPA2 gene product and a pharmaceutically acceptable carrier, and optionally a growth hormone. In another aspect, the administration of growth hormone to the subject may occur simultaneously with the administration of the PAPPA2 gene or gene product, sequentially with the administration of the PAPPA2 gene or gene product, or both.

In one aspect, a method of determining whether an individual is a candidate for treatment of short stature via administration of a functional PAPPA2 gene product or a recombinant vector containing a nucleic acid sequence that encodes said functional PAPPA2 gene product is disclosed. In this aspect, the method may comprise the step of determining the presence of a PAPPA2 functional mutation, wherein, if a functional mutation of PAPPA2 is identified, said individual is a candidate for IGF-1 treatment. In this aspect, the method may further comprise the step of determining whether the individual has a height of −1 SDS, or −2 SDS, or −3 SDS, or greater than −3SDS as compared to an individual of normal stature or a height of 1 SDS, or 2 SDS, or 3 SDS, or greater than 3SDS below the mid-parental target height.

In one aspect, the method may further comprise the step of assaying for increased IGF-1 levels.

Compositions

In one aspect, a composition comprising a therapeutically effective amount of PAPPA2 protein and a pharmaceutically acceptable carrier is disclosed. In a further aspect, a composition consisting essentially of a therapeutically effective amount of PAPPA2 protein and a pharmaceutically acceptable carrier is disclosed. In one aspect, the composition may further comprise a therapeutically effective amount of growth hormone. In a further aspect, the composition may consist essentially of a therapeutically effective amount of PAPPA2 protein, a therapeutically effective amount of growth hormone, and a pharmaceutically acceptable carrier.

The compositions may contain PAPPA2 protein in an amount greater than about 0.5 ng/ml, or greater than about 1.0 ng/ml. In other aspects, the PAPPA2 protein may be present in an amount of from about 0.1 mg/mL to about 250 mg/mL, or from about 1 mg/mL to about 200 mg/mL, or from about 5 mg/mL to about 100 mg/mL, or from about 25 mg/mL to about 50 mg/mL. In a yet further aspect, the PAPPA2 protein may be present in an amount greater than about 250 mg/mL.

The composition may be formulated for subcutaneous administration to a subject or intravenous administration to a subject.

In one aspect, the composition may further comprise a buffer selected from citrate buffer, acetate buffer, bicarbonate buffer, phosphate buffer and combinations thereof.

The pharmaceutical formulations suitable for injectable use may include sterile aqueous solutions (where water soluble) or dispersions and sterile powders for the extemporaneous preparation of sterile injectable solutions or dispersion. In all cases, the form is ideally sterile and be fluid. In one aspect, the formulation may contain preservation agents for preventing contamination by microorganisms such as bacteria and fungi. The carrier may be a solvent or dispersion medium containing, for example, water, ethanol, polyol (for example, glycerol, propylene glycol, and polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The preventions of the action of microorganisms can be brought about by various antibacterial and antifungal agents, for example, parabens, chlorobutanol, phenol, benzyl alcohol, sorbic acid, and the like.

The formulations may include isotonic agents, for example, sugars or sodium chloride. Prolonged absorption of the injectable compositions can be brought about by the use in the compositions of agents delaying absorption, for example, aluminum monosterate and gelatin. Sterile injectable solutions may be prepared with various of the other ingredients enumerated above, followed by filter or terminal sterilization. Generally, dispersions may be prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation may be vacuum dried and the freeze-drying technique may be used to yield a powder of the active ingredient plus any additional desired ingredient from previously sterile-filtered solution thereof.

The formulation may contain one or more excipients. Pharmaceutically acceptable excipients which may be included in the formulation are buffers such as citrate buffer, phosphate buffer (such as, for example, monobasic sodium phosphate, dibasic sodium phosphate and combinations thereof), acetate buffer, bicarbonate buffer, amino acids, urea, alcohols, ascorbic acid, phospholipids; proteins, such as serum albumin, collagen, and gelatin; salts such as EDTA or EGTA, and sodium chloride; liposomes; polyvinylpyrolidone; sugars, such as dextran, mannitol, sorbitol, and glycerol; propylene glycol and polyethylene glycol (e.g., PEG-4000, PEG-6000); glycerol; glycine or other amino acids; and lipids. Buffer systems for use with the formulations include citrate; acetate; bicarbonate; and phosphate buffers.

In certain aspects, the formulations may comprise an excipient selected from the group consisting of polyethylene glycol (PEG), PEG-400, arginine, arginine and glutamic acid, proline, gamma-cyclodextrin and combinations thereof.

In certain aspects, the buffer and/or excipient may be present in the formulation at a concentration of between about 1 and about 50% weight/volume (w/v), or between about 2 and about 40% w/v, or between about 3 and about 30% w/v, or between about 4 and about 20% w/v, or between about 5 and about 10% w/v.

In certain aspects, the buffer and/or excipient may be present in the formulation at a concentration of between about 1 and about 500 mM, or between about 10 and about 400 mM, or between about 20 and about 300 mM, or between about 30 and about 250 mM, or between about 40 and about 200 mM, or between about 50 and about 150 mm, or between about 60 and about 100 mM.

The formulation also may contain a non-ionic detergent. Preferred non-ionic detergents include Polysorbate 20, Polysorbate 80, Triton X-100, Triton X-114, Nonidet P-40, Octyl α-glucoside, Octyl β-glucoside, Brij 35, Pluronic, and Tween 20.

For lyophilization of protein and chaperone preparations, the protein concentration may be 0.1-10 mg/mL. Bulking agents, such as glycine, mannitol, albumin, and dextran, can be added to the lyophilization mixture. In addition, possible cryoprotectants, such as disaccharides, amino acids, and PEG, can be added to the lyophilization mixture. Any of the buffers, excipients, and detergents listed above, can also be added.

The route of administration may be oral or parenteral, including intravenous, subcutaneous, intra-arterial, intraperitoneal, ophthalmic, intramuscular, buccal, rectal, vaginal, intraorbital, intracerebral, intradermal, intracranial, intraspinal, intraventricular, intrathecal, intracisternal, intracapsular, intrapulmonary, intranasal, transmucosal, transdermal, or via inhalation.

Administration of the above-described parenteral formulations may be by periodic injections of a bolus of the preparation, or may be administered by intravenous Of intraperitoneal administration from a reservoir which is external (e.g., an i.v. bag) or internal (e.g., a bioerodable implant, a bioartificial organ, or a population of implanted cells that produce the replacement protein). Other useful parenteral delivery systems include ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, and transdermal patch. Any of the formulations described above can administered in these methods.

EXAMPLES

Studies were approved by the Institutional Review Boards at the Hospital Infantil Universitario Niño Jesús and Cincinnati Children's Hospital Medical Center. Written informed consent was obtained from all subjects or their legal guardians. In family two, homozygosity mapping analysis was implemented on genome-wide SNP data using PLINK.[11] Whole exome sequencing was performed at each institution as previously described.[12,13] Recombinant PAPP-A2 and variants thereof were generated by transfection of mammalian cells with wild-type (WT) or mutated cDNAs. Mutated proteins were compared to WT PAPP-A2 in their abilities to proteolytically cleave radiolabeled IGFBP-3, -4 and -5 and by Western blotting following nonreducing or reducing SDS-PAGE. Levels of complex-bound endogenous IGF-I were assayed by neutral size exclusion chromatography and the capacity to form such complexes as described in the literature.[8]

Circulating PAPP-A2, IGF-I, IGF-II, IGFBP-3, IGFBP-5, ALS and fIGF-I levels were measured by ELISAs. The ability of serum IGFs to activate the IGF-IR in vitro (IGF bioactivity) was analyzed using an IGF-I kinase receptor activation assay (KIRA).[14]

Methods
Serum Assays

Bioactive IGF levels were measured by kinase receptor activation assay (KIRA) as previously described.[25,26] Briefly, this assay measures the ability of IGF in serum to phosphorylate the IGF-I receptor (IGF-IR) in an in vitro based model employing human embryonic cells transfected with cDNA of the human IGFR gene. The ability of serum to phosphorylate the IGF-IR in vitro is compared to a serial dilution of IGF-I. This assay also detects IGF-II and pro-IGF-II activation of the IGF-IR (cross-reactivity 12% and 2%, respectively), but the cross-reactivity of proinsulin and insulin is negligible (<1%). Thus, the output of this assay is referred to as IGF bioactivity as both IGF-I and IGF-II can activate the IGF-IR. The detection limit of this assay is less than 0.08 pg/L.

ELISAs were used to measure serum concentrations of acid labile subunit (ALS; Mediagnost, Reutlingen, Germany), IGF-I, free IGF-I, IGFBP-3, IGFBP-5 and PAPP-A2 (Ansh Labs, Webster, Tex., USA). All assays were performed according to the manufacturers' instructions. Briefly, in all determinations, after incubation of the serum samples in a microtiter plate coated with the corresponding antibody, the wells were washed and the enzyme conjugate added. At the end of the incubation period and after washing, a substrate solution was added until the color developed adequately. Measurements were taken at 450 nm with an automatic microplate analyzer.

The PAPP-A2 ELISA employed is a two-site assay based on specific monoclonal antibodies. Epitope mapping of the two antibodies has been published earlier.[27] The catching antibody maps to the SCR3 module and the detecting antibody maps to the SCRI module of PAPP-A2. All SCR modules are located C-terminal to the site of mutations.

Serum insulin concentrations were measured by an immunoradiometric assay from DIAsource ImmunoAssays (Louvain-la-Neuve, Belgium). Samples were dispensed and a $^{125}$I-anti-insulin monoclonal antibody added into the tubes coated with another anti-insulin monoclonal antibody. After incubation and washing, the bound fraction was counted in a gamma-counter.

In all assays, the intra- and inter-assay coefficients of variation were lower than 10%. Normal ranges were obtained by measuring levels in groups of Tanner Stage I or V healthy controls recruited from the clinic at the Hospital Infantl Universitario Nino Jesus (N=50 in each group).

Chromatography for Endogenous IGF-I Complex Profiles

To determine the IGF-I complex profile, we performed neutral chromatography of 300 ul of serum on Superdex 200. Two-ml fractions were collected and those corresponding to the ternary (six fractions), binary (seven fractions) and free IGF-I (one fraction) were collected and dried in a speed vacuum, reconstituted in 100 ul of PBS buffer 0.05 M, NaCl 0.15 M, pH 7.4, BSA 0.5% and IGF-I was extracted by alcohol-acid treatment and cryoprecipitation. The IGF-I concentration in each fraction was then determined by QLIA (Immulite, Siemens).

Mutagenesis

Plasmid constructs encoding variants of human PAPP-A2 were made by overlap extension PCR[28] using human PAPP-A2 cDNA contained in plasmid pPA2[29] as a template. Outer primers were 5'-CTGTATGTGGATGGCACTCAGG-3' (SEQ ID NO:1) and 5'-GCAACTAGAAGGCACAGTC-GAG-3' (SEQ ID NO:2). Overlapping mutated sets of internal primers were 5'-CTTTGACGACGGAGATACT-GCTG-3' (SEQ ID NO:3) and 5'-CAGCAGTATCTC-CGTCGTCAAAG-3' (SEQ ID NO:4) for mutant PAP P-A2

(D643fs), and 5'-AGGATAGAGATTGATGTAGCACTC CTGACTTCTC-3' (SEQ ID NO:5) and 5'-GAGAAGTCA-GGAGTGCTACATCAATCTCTATCCTC-3' (SEQ ID NO:6) for mutant PAPP-A2(A1033V). The mutated fragments were digested with Xba1 and Xho1 and swapped into pPA2 to generate plasmids pPA2(D643fs) and pPA2(A1033V), respectively. Plasmid DNA was prepared by GenElute HP Plasmid Miniprep Kit (Sigma). All constructs were verified by sequence analysis.

Cell Culture and Transfection

Human embryonic kidney 293T cells (293tsA1609neo)[30] were maintained in high-glucose DMEM supplemented with 10% fetal bovine serum, 2 mM glutamine, nonessential amino acids, and gentamicin (Invitrogen). For transient transfection, $6.0 \times 10^6$ cells were plated onto 10-cm dishes and transfected 18 h later by calcium phosphate coprecipitation using 10 μg plasmid DNA.[31] In addition to plasmid constructs encoding PAPP-A2 or mutated variants, constructs encoding human IGFBP-3,[32] human IGFBP-4,[33] or human IGFBP-5[29] were used. Culture supernatants were harvested 48 h post transfection and cleared by centrifugation, or the cells were further cultured in serum free medium (CD293, Invitrogen) to facilitate purification of the secreted proteins. Levels of wild-type PAPP-A2 in the media were determined by a two-site ELISA.[34]

Assays for Proteolytic Activity

Purification of recombinant proteins (IGFBP-3, -4 and -5) was carried out by affinity chromatography on a 1 ml HisTrap HP column (GE Healthcare). Serum-free media were diluted 1:1 in 20 mM $NaH_2PO_4$, 150 mM NaCl, pH 7.4 (PBS) and loaded onto the column with a flow rate of 1 ml/min. The column was washed with 20 column volumes of 50 mM $NaH_2PO_4$, 1 M NaCl, 20 mM imidazole, 0.05% Tween 20, pH 7.4, followed by five column volumes of PBS. The proteins were eluted with 50 mM $NaH_2PO_4$, 300 mM imidazole, pH 7.4, and dialyzed against 20 mM HEPES, 150 mM NaCl, pH 7.4. Prior to iodination, the IGFBPs were further purified by reversed-phase high pressure liquid chromatography (RP-HPLC) on a Discovery BIO Wide Pore C5 column (4×250 mm, Sigma), as described.[35] Protein purity was assessed by SDS-PAGE, and quantification of purified proteins was done by amino acid analysis. The purified IGFBPs were labeled with $^{125}I$ (Amersham Biosciences), and cleavage reactions were carried out as previously described for PAPP-A.[36] In brief, media harvested from cells transfected with empty vector or human PAPP-A2 cDNA or variants thereof were diluted 1:25 and mixed with $^{125}I$-IGFBP-5 (10 nM) in 50 mM Tris-HCl, 100 mM NaCl, 1 mM CaCl2, pH 7.5. For wild-type PAPP-A2, this dilution corresponds to a concentration of 90 pM PAPP-A2 dimer. To assess activity towards IGFBP-3 and -4, culture media were diluted 1:10, corresponding to a PAPP-A2 concentration of 225 pM. Variants of all experiments in which the IGFBPs were preincubated with IGF-I (100 nM; GroPep Bioreagents) prior to the addition of PAPP-A2 were also carried out. Following three hours of incubation at 37° C., the reactions were terminated by the addition of hot SDS-PAGE sample buffer supplemented with 25 mM EDTA. Substrate and cleavage products were separated by nonreducing SDS-PAGE and visualized by autoradiography using a storage phosphor screen (Molecular Dynamics) and a Typhoon imaging system (GE Healthcare). To assess specific activity towards the IGFBPs, cleavage reactions of 6 h were carried out using equimolar concentrations of PAPP-A2 wild-type and mutant PAPP-A2(A1033V).

Western Blot Analysis

Proteins separated by nonreducing or reducing SDS-PAGE were blotted onto a PVDF membrane (Millipore), blocked with 2% Tween 20, and equilibrated in 50 mM Tris-HCl, 500 mM NaCl, 0.1% Tween 20, pH 9.0 (TST). The blots were incubated overnight at room temperature with an antiserum raised against the N-terminal laminin G-like module of PAPP-A2 diluted 1:10,000 in TST containing 0.5% fetal bovine serum.[36] The blots were incubated for one hour at room temperature with polyclonal swine anti-rabbit IgG-HRP (DAKO, P0217) diluted 1:2,000 in TST containing 0.5% fetal bovine serum. All washing between the steps was done with TST. The blots were developed using enhanced chemiluminescence (ECL Prime, GE Healthcare), and images were captured and analyzed using an ImageQuant LAS 4000 instrument (GE Healthcare). For quantification of mutant PAPP-A2 (A1033V), a standard curve was generated based on serial dilutions of wild-type PAPP-A2 of known concentration.

microCT Methods

Teeth were fixed in 4% paraformaldehyde and subjected to Micro-CT analyses (Skyscan 1172, at 70 kV, 9.75 um per pixel, 0.4 in degree rotation). Reconstruction of the raw images was performed using NRecon V1.4.0 software (Skyscan).

Results

Patient Descriptions

Family one consists of four children of Spanish ancestry born to parents with no known consanguinity. Subject II.1 was evaluated at age nine years for short stature with a height 1.7 SDS below her mid-parental target height (50th-75th percentile) and elevated serum IGF-I, ALS and IGFBP-3 concentrations (Table 1).

TABLE 1

Anthropometric and Biochemical Data

| Subject ID | Sex | Gestational Age (weeks) | Birth Weight (kg) | Birth length (cm) | Age at Exam (Years) | Height (cm) | BMI (kg/m$^2$) | HC (SDS) |
|---|---|---|---|---|---|---|---|---|
| | | | | Family 1 | | | | |
| II.1 | F | 37 | 2.19 (−1.49) | 48.0 (−0.07) | 10.3 | 132.2 (−1.10) | 13.9 (−1.52) | −2.03 |
| II.2 | F | 39 | 3.35 (0.44) | 51.0 (0.94) | 7.8 | 129 (0.87) | 14.8 (−0.98) | +0.02 |
| II.3 | M | 35 | 1.99 (−1.27) | 45.0 (−0.55) | 5.7 | 110.4 (−0.96) | 13.4 (−2.03) | −2.19 |
| II.4 | F | 40 | 3.64 (0.96) | 50.0 (0.11) | 3.6 | 103.3 (1.62) | 15.6 (−0.44) | −0.98 |

TABLE 1-continued

Anthropometric and Biochemical Data

Family 2

| | | | | | | | | |
|---|---|---|---|---|---|---|---|---|
| II.1 | F | 40 | 3.26 (−0.61) | 48.3 (−1.30) | 22.2 | 149.3 (−2.16) | 24.9 (0.76) | 0.45 |
| II.2 | F | 40 | 3.57 (−0.01) | 48.3 (−1.30) | 19.8 | 153.9 (−1.45) | 21.7 (−0.01) | 1.06 |
| II.3 | F | 41 | 2.58 (−2.16) | 45.7 (−2.75) | 18.6 | 138.4 (−3.81) | 20.9 (−0.19) | −2.03 |
| II.4* | M | 41 | 2.84 (−1.69) | 47.0 (−2.18) | 13.8 | 139.1 (−2.82) | 26.7 (1.61) | −1.60 |
| II.5 | M | 39.4 | 2.82 (−1.28) | 48.5 (−0.94) | 9.5 | 117.7 (−3.14) | 15.4 (−0.65) | −1.08 |

| | Total IGF-I (μg/L) | Total IGF-II (μg/L) | Bioactive IGF (μg/L) | Free IGF-I (μg/L) | Bio IGF/ Total IGF-I (%) | IGFBP-3 (μg/L) | IGFBP-5 (μg/L) | ALS (U/L) | PAPP-A2 (μg/L) |
|---|---|---|---|---|---|---|---|---|---|
| Family 1 | | | | | | | | | |
| II.1 | 957 | 1198 | 0.87 | 1.39 | 0.09 | 5912 | 997 | 3745 | ND*** |
| II.2 | 340 | 850 | 2.30 | 2.08 | 0.68 | 3696 | 457 | 2588 | 0.13 |
| II.3 | 882 | 1264 | 1.54 | 0.27 | 0.17 | 4850 | 853 | 3625 | ND*** |
| II.4 | 264 | 759 | 3.21 | 2.16 | 1.22 | 3384 | 322 | 2206 | 0.25 |
| Family 2 | | | | | | | | | |
| II.1 | 237 | 763 | 2.31 | 4.34 | 0.97 | 3235 | 179 | 1375 | 0.34 |
| II.2 | 490 | 629 | 3.90 | 8.36 | 0.80 | 3007 | 187 | 1412 | 0.44 |
| II.3* | 1060 | 921 | 3.35 | 1.98 | 0.32 | 4557 | 760 | 2445 | 0.23 |
| II.4** | 935 | 914 | 2.70 | 3.31 | 0.29 | 4792 | 981 | 2959 | 0.42 |
| II.5 | 831 | 946 | 0.98 | 0.35 | 0.12 | 4403 | 645 | 2456 | 0.30 |
| Normal Values | | | | | | | | | |
| Tanner I | 91-225 | 495-911 | ^Prepubertal 1.94 ± 0.15 | 1.58-3.15 | *median 1.23% range | 2206-4200 | 211-707 | 753-2634 | 0.16-2.69 |
| Tanner V | 270-617 | 560-794 | ^Pubertal 2.93 ± 0.15 | 4.89-9.37 | 0.46-2.59%) | 2796-5280 | 293-1023 | 1260-4030 | 0.23-0.80 |

Legend for Table 1.
*This subject is an adult.
**This subject was Tanner stage 2 at the time of exam and biochemical evaluation with 5-6 cc testes.
ND: Not detectable.
***Zero values in the affected patients are expected because of the frameshift mutation resulting in the absence of the target epitopes of the assay.
HC: Head Circumference.
BioIGF: Biologically active IGF.

In Table 1, affected individuals are shaded in light grey. Unaffected individuals are not shaded. Values in parentheses indicate the standard deviation score (SDS) for anthropometric measures. Normal ranges for bioactive IGF are based on Sorensen et al.[24] The normal ratio of bioactive IGF to total IGF-I is based on 95 healthy subjects aged 7 to 25 years. The ratio was not associated with age. Spontaneous GH secretion over eight hours was elevated (4.8; normal 2.8-3.3 ng/ml/8 hrs). Her younger brother's height (Subject II.3) was 1.3 SDS below mid-parental target height, with similar elevations in IGF-I, IGFBP-3 and ALS (Table 1) and spontaneous GH secretion (5.3 ng/ml/8 hrs). Their birth lengths and weights were normal, although smaller than their unaffected sisters (II.2 and II.4; Table 1). Their growth patterns revealed consistent short stature relative to target height, with more prominent growth deceleration as they age. Subtle dysmorphic features consisting of small chins, mild microcephaly (−1.37 & −1.65 SDS at birth; −2.03 & −2.19 SDS at first physical exam) and long fingers and toes were present (FIG. 1A, B). They are prepubertal. Their unaffected sisters are within 1 SDS of their mid-parental target height with normal IGF-I serum concentrations (Table 1). Glycemia was normal on oral glucose tolerance tests, but with mild fasting hyperinsulinemia (15.1 and 27 μU/ml, normal 4-13).

SUPPLEMENTARY TABLE 1

Longitudinal IGF-I and IGFBP-3 Levels in Subject II.3 from Family 2.

| Age (years, months) | IGF-I (ng/ml) | IGFBP-3 (ng/mL) |
|---|---|---|
| 6 y 10 m | 517.3 | |
| 7 y 5 m | 534.3 | |
| 7 y 7 m | 545.6 | 6400 |
| 8 y 6 m | 726.6 | |
| 9 y 0 m | 698.3 | |
| 10 y 10 m | 519 | 7300 |
| 11 y 5 m | 564 | |
| 11 y 10 m | 786 | |
| 12 y 11 m | 702 | 6400 |
| 13 y 2 m | 825 | 3700 |
| 14 y 0 m | 895 | 8700 |
| 15 y 8 m | 1031 | 8100 |
| 18 y | 1060 | |

Family two consists of five children of Palestinian ancestry born to parents of normal stature (mid-parental target height 30th percentile) who are first cousins. Siblings II.3, II.4 and II.5 had significant post-natal growth retardation with high serum IGF-I and IGFBP-3 concentrations. When subject II.3 was evaluated for short stature at age six years ten months, her height was −3.5 SDS below her target height and IGF-I was 517 ng/ml (normal 47-217). An elevated IGFBP-3 level of 6400 ng/ml (normal 2100-4200) was found later. She showed peak GH levels >50 ng/ml on both clonidine and arginine tests. Her growth chart demonstrates progressive growth failure, no discernible pubertal growth spurt and a final adult height of 138·4 cm (−3.81 SDS). She had normal pubertal timing, undergoing menarche at age 13 years nine months, and had elevated IGF-I throughout childhood (Supplementary Table 1; most recent value 1060 ng/ml at age 18 yrs). Two younger brothers also had progressive growth failure. Subject II.4 was evaluated for growth failure at age 12 years six months with an IGF-I level of 657 ng/ml (normal 93-567) despite being pre-pubertal. Subject II.5 was evaluated at age eight years four months with an IGF-I level of 636 ng/ml (normal 49-351). Their peak GH levels after stimulation testing with clonidine and L-Dopa were 14.7 and 37 ng/ml, respectively. Fasting glucose levels were normal in both brothers, with mild hyperinsulinemia in Subject II.4 (17.1 µU/ml) and a normal insulin level of 7 µU/ml in Subject II.5. Subjects II.3 and II.4 were born mildly small for gestational age, but subject II.5 was within the normal range. All three affected siblings had long thin fingers, a small chin, moderate microcephaly (Table 1) and delayed dental eruption.

Skeletal surveys in the two affected siblings from family one and subjects II.4 and II.5 in family two showed no signs of overt skeletal dysplasia; however, thin long bones most prominent in the fibulae, tibiae and femurs were found. Bone age was consistent with chronologic age in all subjects. DXA scans (QDR 4500, Hologic, Waltham, Mass.) were performed on the two affected siblings from family one. Bone mineral density was decreased at the lumbar spine (height adjusted Z-score −2.49 SDS in II.1, −2.0 SDS in II.3).

Micro-CT analysis of a tooth extracted from subject II.1 in family one showed significantly decreased enamel and dentin density. No significant cognitive dysfunction or hearing abnormalities were found in the patients from either family.

Genetic Analysis

Given the two affected siblings of different sex in family one with unaffected parents, Applicant hypothesized that the disorder had an autosomal recessive inheritance pattern. After excluding mutations in the IGF-IR gene, whole exome sequencing was performed in the affected sister (II.1). Applicant searched for genes with either a single homozygous or two heterozygous rare (minor allele frequency <1%) nonsynonymous variants present. Five genes met these criteria (Supplementary Table 2), four of which fell within a block of homozygosity on chromosome one, suggesting that the parents have a distant common ancestor. The novel homozygous frameshift mutation in PAPPA2 (c.1927_1928insAT, p.D643fs25*) was highlighted as the likely causal variant, given the loss of function nature of the mutation and the role of the encoded protein, PAPP-A2, in cleaving IGFBPs. This variant was confirmed via Sanger sequencing to be homozygous in both affected individuals, heterozygous in both parents and one unaffected sibling (II.4) and absent in the second unaffected sibling (II.2) (FIG. 2).

SUPPLEMENTARY TABLE 2

Candidate Genes Based on Exome Sequencing Analysis in Family 1.

| Chr. | Position | Reference allele | Variant allele | Genotype | Gene | cDNA change | Protein change | Minor allele frequency |
|---|---|---|---|---|---|---|---|---|
| 1 | 158152680 | C | T | Homozygous | CD1D | NM_001766 c.C620T | A207V | Novel |
| 1 | 158651382 | G | A | Homozygous | SPTA1 | NM_003126 c.C466T | R156W | 0.0001243 |
| 1 | 161021465 | G | C | Homozygous | ARHGAP30 | NM_001025598 c.C1059G | S353R | 0.0000182 |
| 1 | 176564667 | — | insAT | Homozygous | PAPPA2 | NM_020318 c.1927_1928insAT | D643fs25* | Novel |
| 10 | 134699337 | G | A | Heterozygous | TTC40 | NM_001200049 c.C3431T | T1144M | 0.0002229 |
| 10 | 134738299 | G | A | Heterozygous | TTC40 | NM_001200049 c.C1157T | T386M | 0.0001469 |

Chr.—Chromosome.
Minor allele frequency was taken from the ExAC Browser http://exac.broadinstitute.org Due to the known consanguinity in family two, Applicant assumed that the affected children were homozygous carriers of a rare autosomal recessive variant causal for their growth retardation. Genome-wide genotyping performed in the three affected children identified four large (>6 MB) shared regions of homozygosity (Supplementary Table 3). Whole exome sequencing was performed on Patient II.3.

SUPPLEMENTARY TABLE 3

Regions of homozygosity in Family 2

| Chromosome | Start Position | End Position | Length (MB) |
|---|---|---|---|
| 1 | 171755170 | 178019772 | 6.3 |
| 3 | 186205930 | 194753890 | 8.5 |
| 8 | 54308719 | 61809918 | 7.5 |
| 13 | 74096953 | 84845106 | 10.7 |

Analysis focused on rare homozygous nonsynonymous variants within the shared regions of homozygosity. Two novel missense variants met these criteria, only one of which segregated in the family (FIG. 2): a novel missense variant in PAPPA2 (c.3098C>T, p.Ala1033Val). Neither of the two PAPPA2 variants was found in public databases representing more than 60,000 exomes and including at least 700 individuals from Spain (http://exac.broadinstitute.org/, http://evs.gs.washington.edu/EVS/, http://geevs.crg.eu/, http://bioinfo.cipf.es/apps-beta/exome-server/beta/). Notably, there are no individuals in these large datasets with homozygous loss-of-function variants of the PAPPA2 gene. Thus, the genetic analyses of these two families identified two novel nonsynonymous mutations in PAPPA2 as the likely causal variants.

In Vitro Functional Effects of Mutations in PAPPA2

Figure 3A:
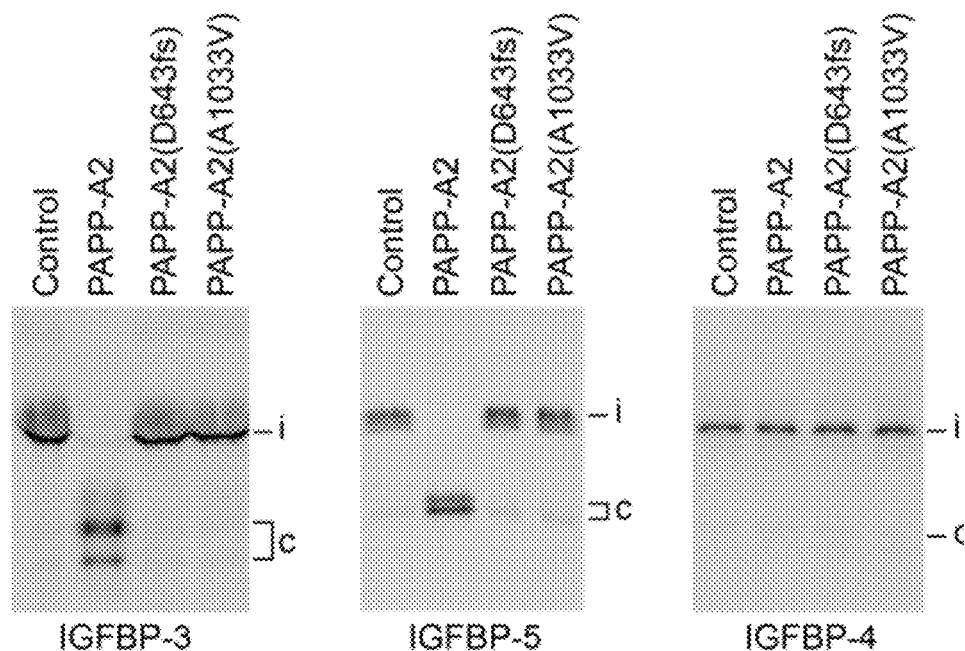
FIG. 3A-C depict in vitro characterization of mutated PAPP-A2.

PAPP-A2 is a metalloproteinase that specifically cleaves IGFBP-3 and -5.[10] To assess the consequences of our subjects' mutations on PAPP-A2 proteolytic function, recombinant variants were compared with WT PAPP-A2 following transfection of HEK 293 cells. Media from cells transfected with cDNA encoding the D643fs or A1033V variants showed no proteolytic activity towards IGFBP-3 or -5 under conditions where media from cells transfected with WT PAPP-A2 cDNA completely cleaved these substrates (FIG. 3A).

Figure 3B:
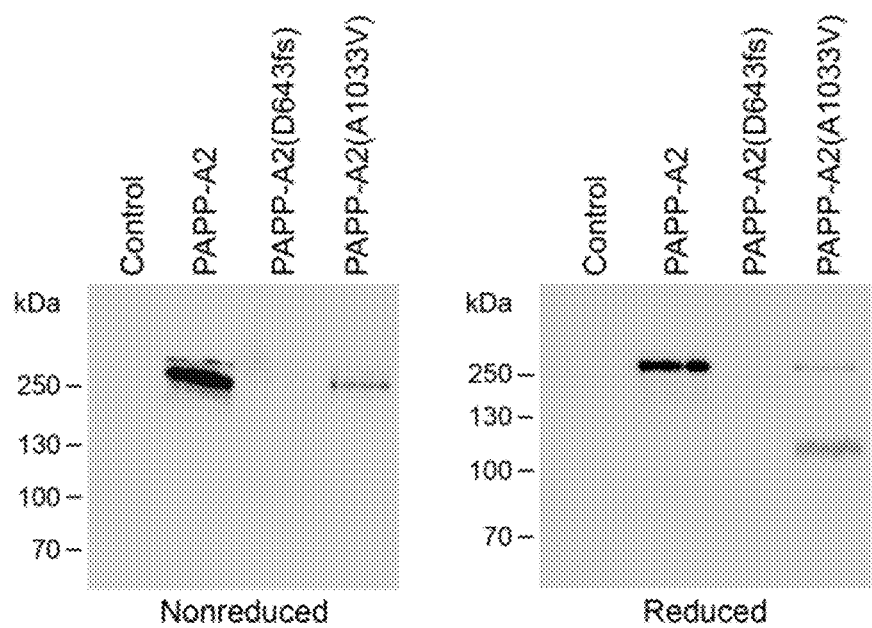
Figure 3C:
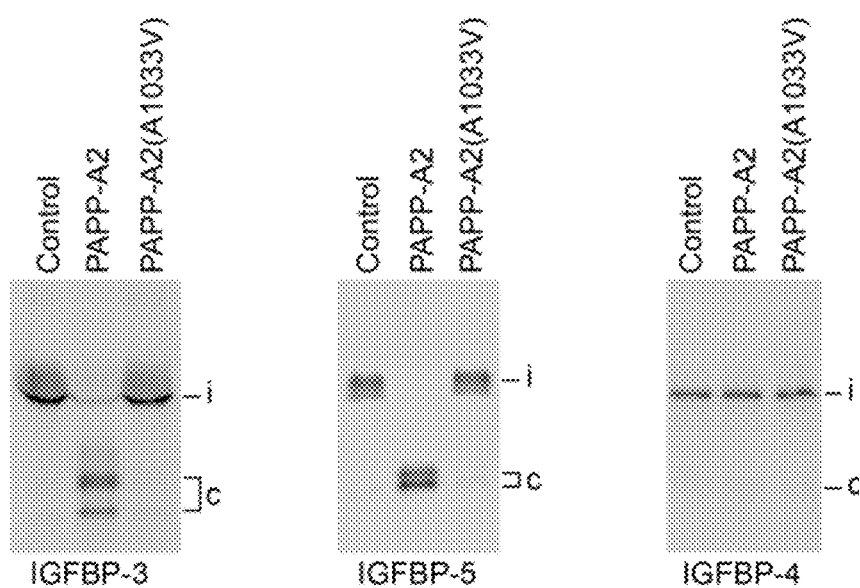

As expected, none of the variants cleaved the PAPP-A substrate, IGFBP-4. Western blotting showed a complete lack of expression for the D643fs mutant (as would be expected with a severely truncated protein), while expression of A1033V was markedly reduced compared to WT PAPP-A2. Upon reduction of disulfide bonds, two bands appeared for A1033V, probably caused by partial intramolecular cleavage (FIG. 3B). To further analyze the A1033V mutant, samples were adjusted for the reduced expression of this variant and, at equimolar concentrations (FIG. 3C), it still showed no activity, suggesting that neither full-length A1033V nor proteolytically cleaved A1033V is capable of cleaving the IGFBPs.

In Vivo Evaluation of IGF-I and IGFBPs

To further delineate the in vivo consequences of our subjects' mutations on IGF-I physiology, Applicant measured serum PAPP-A2 levels. As expected, subjects in family one homozygous for the D463fs truncating mutation had no detectable PAPP-A2 (Table 1). In family two, PAPP-A2 levels were detectable at the low end of the normal range, but with no difference between the affected individuals and their heterozygous siblings.

Serum concentrations of total IGF-I were extremely elevated in all affected subjects and normal in their unaffected siblings (Table 1). IGFBP-3 concentrations were above the normal range in the four younger patients and in the upper normal range in the Tanner V subject of family two. ALS levels were elevated in three of five subjects and in the upper limits of normal in two. IGFBP-5 levels were elevated in four of five patients. IGF-II levels were elevated in all five patients (Table 1). As PAPP-A2 cleaves IGFBP-3 and -5 thereby releasing IGF-I from the ternary complex, we hypothesized that fIGF-I levels would be decreased in the affected subjects, despite the elevated total IGF-I levels. Indeed, fIGF-I levels were low in four of five patients (Table 1), suggesting that they have a functional defect in the ability to liberate IGF-I from its binding partners. To substantiate this finding by an independent method, the potential of the patients' serum to stimulate the IGF-IR in vitro was assessed. IGF bioactivity was lower in the three prepubertal patients compared to unaffected prepubertal subjects, with the percentage of bioactive IGF (bioactive IGF/total IGF-I) reduced in all affected patients (Table 1).

To further confirm that defects in PAPP-A2 function can cause this unique phenotype, Applicant demonstrated that mice carrying a targeted deletion of Pappa2[11] also have markedly decreased fIGF-I levels, despite a >50% increase in total IGF-I levels (Supplementary Table 4). Lastly, measurement of the amount of IGF-I bound in ternary complexes in the serum of subjects of family one showed a marked increase in IGF-I as part of the ternary complex in all affected subjects (FIG. 4A). Moreover, in these patients the overall capacity to form ternary complexes was greatly increased compared to prepubertal controls (Expanded View FIG. 2A,B).

SUPPLEMENTARY TABLE 4

Total and Free IGF-Levels in Pappa2 Knock Out Mice (16 weeks of age)

|  | Total IGF-I (ng/ml) | Free IGF-I (ng/ml) |
| --- | --- | --- |
| Male Wild Type (N = 9) | 28 ± 2.6 | 5.7 ± 0.98 |
| Male Knock Out (N = 8) | 44 ± 1.4 | 0.2 ± 0.08 |
| P-value for comparison between groups | 0.0001 | 0.0012 |
| Female Wild Type (N = 12) | 27 ± 2.3 | 6.6 ± 1.40 |
| Female Knock Out (N = 7) | 43 ± 3.7 | 0.3 ± 0.17 |
| P-value for comparison between groups | <0.0001 | <0.0001 |

Example: PAPP-A2 Enzyme Replacement Therapy Using Plasma Transfusion

We have an IRB approved protocol for performing genetic studies in patients with unexplained growth disorders. As part of that protocol, we studied a family who currently lives in New York. They have three children (1 daughter and 2 sons) with short stature, all of whom have very elevated IGF-1 (insulin like growth factor 1 levels) as well as elevated IGF binding protein 3 (IGFBP-3) levels. The parents are first cousins of Palestinian descent. Additionally, they have two daughters who are unaffected. IGF-1 is the main mediator of growth hormone action and circulates bound to IGFBP-3 (and other IGF binding proteins). It is extremely unusual to have an elevated IGF-1 and/or IGFBP-3 level in the setting of short stature. The eldest affected daughter is 18 years old and has completed growing at 138.3 cm (4'6", −3.82SD). Her 13 and 9 year old brothers are −2.68 and -2.72 standard deviations for height. We performed homozygosity mapping followed by exome sequencing and identified 2 rare homozygous nonsynonymous variants that were shared by the three affected siblings. Only one of these variants segregated with the phenotype in the rest of the family, a novel missense mutation in PAPPA2 (Ala1033Val). Thus, based on genetic grounds alone, we only identified a single candidate variant in the entire exome.

PAPP-A2 is a plasma protease that is known to cleave IGFBP-3 and IGFBP-5. It is thought that this cleavage frees up IGF-1 from its bound form allowing it to become the active free IGF-1. Our hypothesis is that loss of activity of PAPP-A2 leads to an inability to cleave the IGF binding proteins and thus an overall elevation in IGFBP-3 and consequent elevation in total IGF-1. However, this IGF-1 cannot be freed up and is thus not able to be active leading to short stature. Our patients' missense variant is predicted to be damaging by in silico prediction models such as Polyphen2. Furthermore, two knock out mouse models of PAPPA2 as well as a zebrafish knock out exist, all showing growth retardation (post-natally in the mice). Finally, and most importantly, a second family with a homozygous frameshift mutation in PAPPA2 has been identified leading to the exact same clinical and biochemical phenotype as our patients. Taken together, this is definitive evidence that our patients' mutation in PAPPA2 is responsible for their short stature phenotype.

The older sister has been treated with growth hormone and recombinant IGF-1 in the past, both without any significant improvement in height. It is believed that growth hormone would just further increase IGF-1 and IGFBP-3 levels but would not allow for IGF-1's release due to the defect in PAPP-A2. Similarly, recombinant IGF-1 would get bound by the IGFBP-3. Therefore, it is hypothesized that PAPP-A2 enzyme replacement therapy could improve growth in these patients by freeing IGF-1 from its binding proteins. Because recombinant PAPP-A2 is not currently available as a drug, routine plasma transfusion was proposed as a means of replacing PAPP-A2 in our patients. FFP transfusion used to be routinely used for coagulation factor replacement. Furthermore, genetic defects in ADAMTS13, a zinc-dependent plasma protease, leads to congenital thrombotic thrombocytopenic purpura. This is treated using plasma transfusion as a means of enzyme replacement. PAPP-A2 is also a zinc-dependent plasma protease and should in theory be replaceable by plasma transfusion.

In order to pursue a therapeutic trial of PAPP-A2 enzyme replacement therapy via plasma transfusion, it would be ideal to know the pharmacokinetic and pharmacodynamics parameters of PAPP-A2. However, there is no data about any pharmacokinetic or pharmacodynamics parameters of PAPP-A2 in humans or in any model organism, including mice. The half-life of PAPP-A2 is unknown. PAPP-A2 is a plasma protein found in low levels in all people. The levels become elevated in pregnancy and its role in pregnancy and the developing fetus is not well understood. PAPP-A2 levels were measured in our patients using a commercially available ELISA (Ansh Labs) and were in the low normal range (0.12, 0.27 and 0.27 ng/ml in the sister and two brothers respectively). The normal ranges for a pre-pubertal child are 0.16-2.69 ng/ml and a post-pubertal child 0.23-0.8 ng/ml. These normal ranges were obtained from our colleague in Madrid who is studying PAPP-A2 in healthy children. The affected sister has completed puberty. We then obtained 15 samples of Fresh Frozen Plasma (FFP) as well as 15 samples of cryoprecipitate from the Hoxworth Blood Bank. We measured PAPP-A2 levels in the FFP and cryoprecipitate. PAPP-A2 was detectable in all the FFP samples with a mean value of 0.28+/−0.06 ng/ml (note the very tight standard deviation). Levels in cryoprecipitate were not significantly elevated and were much more variable thus making it a less useful transfusion agent.

In theory, it would be ideal to perform a formal pharmacokinetic study of PAPP-A2 in humans. However, our patients have a missense mutation with detectable protein levels. The PAPP-A2 assay is not able to distinguish between our patient's protein and the normal functioning protein. Therefore, we would need to be able to detect a significant rise in PAPP-A2 above our patient's baseline level. This may not be possible using the current PAPP-A2 ELISA. Consider the following calculation:

Plasma volume approximates 50 cc/kg. If we infuse 20 cc/kg of FFP (the maximum reasonable amount to give in a single transfusion), this should increase the plasma level of PAPP-A2 by 40% of the level in the FFP transfusion (20/50). 0.4×0.28 ng/ml (the mean FFP PAPP-A2 level)=0.11. The analytical sensitivity of the PAPP-A2 ELISA is 0.07 ng/ml which is very close to the expected increase in functional PAPP-A2. As such, a successful pharmacokinetic study may not be feasible.

A focused study of the pharmacodynamics effects of PAPP-A2 replacement via plasma transfusion was performed in the 18 year old sister who affected by the same mutation. Her current IGF-1 and IGFBP-3 levels are quite elevated and she should represent a good model for the effects of PAPP-A2 replacement on IGF-1 and IGFBP-3 levels.

PRIMARY OUTCOME: We are pre-specifying a decrease in either total IGF-1 or IGFBP-3 of 20% or greater as a clinically meaningful decrease in levels. If there is a decrease of 10-19% in both IGF-1 and IGFBP-3, this will also be considered to be clinically meaningful. Changes in levels less than 10% will not be considered clinically meaningful.

This was an n=1 study which will serve as a proof of principle that plasma transfusion can be used for PAPP-A2 enzyme replacement therapy. A single simple plasma transfusion was performed and pharmacokinetic and pharmacodynamics parameters were measured.

A 20 cc/kg transfusion of FFP was given over 3 hours on day 0. A 3 cc sample of the FFP was taken to measure PAPP-A2 levels. The patient was observed for an additional 2 hours to watch for an immediate transfusion reaction. Blood samples were then obtained. All blood samples from days −1 through day 14 were batched and run after the Day 14 sample was collected.

| Lab | Day −1 | Day 0 | Day 1 | Day 3 | Day 7 | Day 11 | Day 14 | Day 21 | Day 28 |
|---|---|---|---|---|---|---|---|---|---|
| Blood type and cross | X | | | | | | | | |
| CBC | X | | | | | | | | |
| IGF-1 | X | X | X | X | X | X | X | X | X |
| IGFBP-3 | X | X | X | X | X | X | X | X | X |
| Free IGF-1 | X | X | X | X | X | X | X | X | X |
| PAPP-A2 | X | X | X | X | X | X | X | X | X |
| Serum for storage | X | X | X | X | X | X | X | X | X |
| FFP aliquot | | X | | | | | | | |
| Urine HCG | X | | | | | | | | |

Samples for Days 11, 14, 21, and 28 can be done +/−1 day for scheduling convenience. The CBC and Blood Type will be sent to the routine CCHMC clinical lab. IGF-1 and IGFBP-3 will be performed in the clinical Endocrine Lab using the IDS-iSYS Immunoassays. Free IGF-1 and PAPP-A2 levels will be performed at Ansh Labs. Free IGF-1 is not used as a primary outcome as it is not clinically validated. An additional 10 cc of blood was obtained with each sample for future analysis.

Results

| Sample | Bioactive IGF-I (ng/mL) | Total IGF-I (ng/mL) | PAPP-A2 (ng/mL) |
|---|---|---|---|
| P1 D1 Plasma | 2.955 | 805.4 | 0.155 |
| P1 D3 Plasma | 4.075 | 818.7 | <0.122 |
| P1 D7 Plasma | 3.278 | 1055.875 | <0.122 |
| P1 D11 Plasma | 1.831 | 690.275 | 0.146 |
| P1 D14 Plasma | 2.116 | 732.125 | 0.216 |
| P1 d-0 Plasma | 0.966 | 697.375 | <0.122 |
| P1 d-1 Plasma | 1.516 | 783.7 | 0.127 |
| P2 Plasma | 2.831 | 720.4 | 0.261 |

| Sample | Bioactive IGF-I (ng/mL) | Total IGF-I (ng/mL) | PAPP-A2 (ng/mL) |
| --- | --- | --- | --- |
| P3 Plasma | n/a | 437.275 | 0.228 |
| P1 D1 Serum | 4.453 | 928.95 | 0.233 |
| P1 D3 Serum | 3.664 | 329.325 | 0.182 |
| P1 D7 Serum | 3.327 | 1409 | 0.173 |
| P1 D11 Serum | 2.884 | 804.625 | 0.19 |
| P1 D14 Serum | 2.44 | 984.425 | 0.245 |
| P1 d-0 Serum | 1.761 | 921.15 | 0.237 |
| P1 d-1 Serum | 1.714 | 948.125 | 0.309 |
| P2 Serum | 5.264 | 790.35 | 0.309 |
| P3 Serum | 3.178 | 560.375 | 0.359 |
| FFP A | 1.854 | 328.95 | 0.207 |
| FFP B | 9.302 | 265.15 | 0.269 |
| FFP C | 9.862 | 203.225 | 0.141 |
| FFP D | 10.728 | 102.25 | 0.309 |

In the Table above, P1 is the subject who underwent the plasma transfusion trial. P2 and P3 are her two affected brothers. The FFP samples are aliquots of fresh frozen plasma taken from the units which were transfused into P1. The transfusion did not result in a measurable increase in PAPPA2 levels in P1. However, despite this fact, the free IGF-1 levels transiently increased from baseline (days −1, 0) to twice the baseline values for the first 7 days of the experiment. They then began falling. There was no significant change in the total IGF-1 levels throughout the trial. These results provide supportive evidence that administering even a small amount of PAPPA2 may increase the proportion of fIGF1.

REFERENCES

1. Baxter R C. Insulin-like growth factor (IGF)-binding proteins: interactions with IGFs and intrinsic bioactivities. American journal of physiology Endocrinology and metabolism 2000; 278(6): E967-76.
2. Yakar S, Rosen C J, Beamer W G, et al. Circulating levels of IGF-1 directly regulate bone growth and density. The Journal of clinical investigation 2002; 110(6): 771-81.
3. David A, Hwa V, Metherell L A, et al. Evidence for a continuum of genetic, phenotypic, and biochemical abnormalities in children with growth hormone insensitivity. Endocrine reviews 2011; 32(4):472-97.
4. Amselem S, Duquesnoy P, Attree O, et al. Laron dwarfism and mutations of the growth hormone-receptor gene. The New England journal of medicine 1989; 321(15): 989-95.
5. Kofoed E M, Hwa V, Little B, et al. Growth hormone insensitivity associated with a STAT5b mutation. The New England journal of medicine 2003; 349(12): 1139-47.
6. Woods K A, Camacho-Hubner C, Savage M O, Clark A J. Intrauterine growth retardation and postnatal growth failure associated with deletion of the insulin-like growth factor I gene. The New England journal of medicine 1996; 335(18): 1363-7.
7. Abuzzahab M J, Schneider A, Goddard A, et al. IGF-I receptor mutations resulting in intrauterine and postnatal growth retardation. The New England journal of medicine 2003; 349(23): 2211-22.
8. Domene H M, Bengolea S V, Martinez A S, et al. Deficiency of the circulating insulin-like growth factor system associated with inactivation of the acid-labile subunit gene. The New England journal of medicine 2004; 350(6): 570-7.
9. Begemann M, Zirn B, Santen G, et al. Paternally Inherited IGF2 Mutation and Growth Restriction. The New England journal of medicine 2015; 373(4): 349-56.
10. Overgaard M T, Boldt H B, Laursen L S, Sottrup-Jensen L, Conover C A, Oxvig C. Pregnancyassociated plasma protein-A2 (PAPP-A2), a novel insulin-like growth factor-binding protein-5 proteinase. The Journal of biological chemistry 2001; 276(24): 21849-53.
11. Conover C A, Boldt H B, Bale L K, et al. Pregnancy-associated plasma protein-A2 (PAPP-A2): tissue expression and biological consequences of gene knockout in mice. Endocrinology 2011; 152(7): 2837-44.
12. Oxvig C. The role of PAPP-A in the IGF system: location, location, location. Journal of cell communication and signaling 2015.
13. Bayes-Genis A, Conover C A, Overgaard M T, et al. Pregnancy-associated plasma protein A as a marker of acute coronary syndromes. The New England journal of medicine 2001; 345(14): 1022-9.
14. Malone F D, Canick J A, Ball R H, et al. First-trimester or second-trimester screening, or both, for Down's syndrome. The New England journal of medicine 2005; 353(19): 2001-11.
15. Christians J K, de Zwaan D R, Fung S H. Pregnancy associated plasma protein A2 (PAPP-A2) affects bone size and shape and contributes to natural variation in postnatal growth in mice. PloS one 2013; 8(2): e56260.
16. Yan X, Baxter R C, Firth S M. Involvement of pregnancy-associated plasma protein-A2 in insulinlike growth factor (IGF) binding protein-5 proteolysis during pregnancy: a potential mechanism for increasing IGF bioavailability. The Journal of clinical endocrinology and metabolism 2010; 95(3): 1412-20.
17. Kjaer-Sorensen K, Engholm D H, Jepsen M R, et al. Papp-a2 modulates development of cranial cartilage and angiogenesis in zebrafish embryos. Journal of cell science 2014; 127(23): 5027-37.
18. Zhang M, Xuan S, Bouxsein M L, et al. Osteoblast-specific knockout of the insulin-like growth factor (IGF) receptor gene reveals an essential role of IGF signaling in bone matrix mineralization. The Journal of biological chemistry 2002; 277(46): 44005-12.
19. Modric T, Silha J V, Shi Z, et al. Phenotypic manifestations of insulin-like growth factor-binding protein-3 overexpression in transgenic mice. Endocrinology 2001; 142(5): 1958-67.
20. Christians J K, Hoeflich A, Keightley P D. PAPPA2, an enzyme that cleaves an insulin-like growthfactor-binding protein, is a candidate gene for a quantitative trait locus affecting body size in mice. Genetics 2006; 173(3): 1547-53.
21. Lango Allen H, Estrada K, Lettre G, et al. Hundreds of variants clustered in genomic loci and biological pathways affect human height. Nature 2010; 467(7317): 832-8.
22. Wood A R, Esko T, Yang J, et al. Defining the role of common variation in the genomic and biological architecture of adult human height. Nature genetics 2014; 46(11): 1173-86.
23. Kloverpris S, Gaidamauskas E, Rasmussen L C, et al. A robust immunoassay for pregnancy associated plasma protein-A2 based on analysis of circulating antigen: establishment of normal ranges in pregnancy. Molecular human reproduction 2013; 19(11): 756-63.
24. Sorensen J S, Birkebaek N H, Bjerre M, et al. Residual beta-cell function and the insulin-like growth factor system in Danish children and adolescents with type 1 diabetes. The Journal of clinical endocrinology and metabolism 2015; 100(3): 1053-61.
25. Chen J W, Ledet T, Orskov H, et al. A highly sensitive and specific assay for determination of IGF-I bioactivity in human serum. American journal of physiology Endocrinology and metabolism 2003; 284(6): E1149-55.
26. Reinhard M, Frystyk J, Jespersen B, et al. Effect of hyperinsulinemia during hemodialysis on the insulin-like growth factor system and inflammatory biomarkers: a randomized open-label crossover study. BMC nephrology 2013; 14: 80.
27. Kloverpris S, Gaidamauskas E, Rasmussen L C, et al. A robust immunoassay for pregnancy-associated plasma protein-A2 based on analysis of circulating antigen: establishment of normal ranges in pregnancy. Molecular human reproduction 2013; 19(11): 756-63.
28. Ho S N, Hunt H D, Horton R M, Pullen J K, Pease L R. Site-directed mutagenesis by overlap extension using the polymerase chain reaction. Gene 1989; 77(1): 51-9.
29. Overgaard M T, Boldt H B, Laursen L S, Sottrup-Jensen L, Conover C A, Oxvig C. Pregnancy-associated plasma protein-A2 (PAPP-A2), a novel insulin-like growth factor-binding protein-5 proteinase. The Journal of biological chemistry 2001; 276(24): 21849-53.
30. Pear W S, Nolan G P, Scott M L, Baltimore D. Production of high-titer helper-free retroviruses by transient transfection. Proceedings of the National Academy of Sciences of the United States of America 1993; 90(18): 8392-6.
31 Overgaard M T, Haaning J, Boldt H B, et al. Expression of recombinant human pregnancy-associated plasma protein-A and identification of the proform of eosinophil major basic protein as its physiological inhibitor. The Journal of biological chemistry 2000; 275(40): 31128-33.
32. Laursen L S, Oxvig C. Real-time measurement in living cells of insulin-like growth factor activity using bioluminescence resonance energy transfer. Biochemical pharmacology 2005; 69(12): 1723-32.
33. Boldt H B, Overgaard M T, Laursen L S, Weyer K, Sottrup-Jensen L, Oxvig C. Mutational analysis of the proteolytic domain of pregnancy-associated plasma protein-A (PAPP-A): classification as a metzincin. The Biochemical journal 2001; 358(Pt 2): 359-67.
34. Laursen L S, Kjaer-Sorensen K, Andersen M H, Oxvig C. Regulation of insulin-like growth factor (IGF) bioactivity by sequential proteolytic cleavage of IGF binding protein-4 and -5. Molecular endocrinology 2007; 21(5): 1246-57.
35. Gyrup C, Oxvig C. Quantitative analysis of insulin-like growth factor-modulated proteolysis of insulin-like growth factor binding protein-4 and -5 by pregnancy-associated plasma protein-A. Biochemistry 2007; 46(7): 1972-80.
36. Winn V D, Gormley M, Paquet A C, et al. Severe preeclampsia-related changes in gene expression at the maternal-fetal interface include sialic acid-binding immunoglobulin-like lectin-6 and pappalysin-2. Endocrinology 2009; 150(1): 452-62.

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of treating progressive growth failure in a human subject diagnosed with idiopathic short stature and having a mutation in PAPP-A2, comprising administering plasma containing a PAPP-A2 enzyme intravenously to said human subject;

wherein said PAPP-A2 mutation is a homozygous loss-of-function mutation selected from D643fs25*, Ala1033Val, or a combination thereof;

wherein said mutation causes elevated serum levels of total IGF-I in said subject;

wherein said PAPP-A2 enzyme administered to said subject does not contain said homozygous loss-of-function mutation selected from D643fs25*, Ala1033Val, or a combination thereof; and wherein said administration increases free IGF1 (fIGF1) in said subject.

2. The method of claim 1, wherein said human subject is identified as small for gestational age without catch up growth.

3. The method of claim 1, wherein said subject is administered said plasma during puberty, prior to puberty, or both.

4. The method of claim 1, where said human subject has a height of about two standard deviations below the mid-parental target height.

5. The method of claim 1, comprising co-administering a growth hormone to said subject.

6. The method of claim 5, wherein said growth hormone is co-administered at a time period selected from one or both of simultaneously and sequentially.

* * * * *

SEQUENCE LISTING

<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Primer

<400> SEQUENCE: 1
ctgtatgtgg atggcactca gg                                              22

<210> SEQ ID NO 2

```
<211> LENGTH: 22
<212> TYPE: DNA
<213> ORGANISM: Artificial Sequence
<220> FEATURE:
<223> OTHER INFORMATION: Primer

<400> SEQUENCE: 2
gcaactagaa ggcacagtcg ag                                          22

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
ctttgacgac ggagatactg ctg                                         23

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
cagcagtatc tccgtcgtca aag                                         23

<210> SEQ ID NO 5
<211> LENGTH: 34
<212> TYPE: DNA
<213> ORGANISM: Artificial Sequence
<220> FEATURE:
<223> OTHER INFORMATION: Primer

<400> SEQUENCE: 5
aggatagaga ttgatgtagc actcctgact tctc                             34

<210> SEQ ID NO 6
<211> LENGTH: 35
<212> TYPE: DNA
<213> ORGANISM: Artificial Sequence
<220> FEATURE:
<223> OTHER INFORMATION: Primer

<400> SEQUENCE: 6
gagaagtcag gagtgctaca tcaatctcta tcctc                            35
```